(12) United States Patent
Rajopadhye et al.

(10) Patent No.: US 8,685,370 B2
(45) Date of Patent: Apr. 1, 2014

(54) INTEGRIN TARGETING AGENTS AND IN-VIVO AND IN-VITRO IMAGING METHODS USING THE SAME

(75) Inventors: Milind Rajopadhye, Westford, MA (US); Guojie Ho, Sudbury, MA (US); Bohumil Bednar, Chalfont, PA (US); Le T. Duong, Lansdale, PA (US); Paul J. Coleman, Harleysville, PA (US)

(73) Assignees: Visen Medical, Inc., Bedford, MA (US); Merck & Co., Inc., Rahway, NJ (US)

( * ) Notice: Subject to any disclaimer, the term of this patent is extended or adjusted under 35 U.S.C. 154(b) by 548 days.

(21) Appl. No.: 12/922,594

(22) PCT Filed: Mar. 13, 2009

(86) PCT No.: PCT/US2009/037114
§ 371 (c)(1),
(2), (4) Date: Feb. 4, 2011

(87) PCT Pub. No.: WO2009/114776
PCT Pub. Date: Sep. 17, 2009

(65) Prior Publication Data
US 2011/0165075 A1    Jul. 7, 2011

Related U.S. Application Data

(60) Provisional application No. 61/036,495, filed on Mar. 14, 2008.

(51) Int. Cl.
*A61K 49/00*    (2006.01)
(52) U.S. Cl.
USPC ......... 424/9.1; 424/1.11; 424/1.65; 424/1.73; 424/9.6
(58) Field of Classification Search
USPC ........... 424/1.11, 1.65, 1.69, 1.81, 1.85, 1.89, 424/9.1, 9.2, 9.3, 9.4, 9.5, 9.6, 9.7, 9.8; 514/1, 1.1; 530/300; 546/1, 152, 184, 546/249
See application file for complete search history.

(56) References Cited

FOREIGN PATENT DOCUMENTS

| WO | WO-99/31099 A1 | 6/1999 |
|----|----------------|--------|
| WO | WO-2005/082889 A1 | 9/2005 |

OTHER PUBLICATIONS

Hutchinson et al (J. Med. Chem, 2003, vol. 46, No. 22, pp. 4790-4798).*
P. Raboisson et al., "Identification of novel short chain 4-substituted indoles as potent avb3 antagonist using structure-based drug design," European Journal of Medicinal Chemistry, 42 (2007) 334-343.
M.J. Breslin et al., "Nonpeptide avb3 antagonists. Part 10: In vitro and in vivo evaluation of a potent 7-methyl substituted tetrahydro-[1,8]naphthyridine derivative," Bioorganic & Medicinal Chemistry Letters 14 (2004) 4515-4518.
Cui D et al.; In vitro and in vivo metabolism of a potent and selective integrin [alpha] v [beta]3 antagonist in rats, dogs, and monkeys; Drug Metabolism and Disposition 200408; vol. 32, No. 8; Aug. 2004; pp. 848-861; XP002581904; ISSN: 0090-9556, (only abstract was submitted).
Burnett C. A. et al.; Synthesis, in vitro, and in vivo characterization of an integrin alphavbeta3-targeted molecular probe for optical imaging of tumor; Bioorganic & Medicinal Chemistry; Pergamon; vol. 13, No. 11; Jun. 1, 2005; pp. 3763-3771; XP004873535; ISSN: 0968-0896, (only abstract was submitted).
Coleman P. J. et al.; Nonpeptide [alpha] v [beta]3 antagonists. Part 11: Discovery and preclinical evaluation of potent [alpha] v [beta] 3 antagonists for the prevention and treatment of osteoporosis; Journal of Medicinal Chemistry 20040923; vol. 47, No. 20; Sep. 23, 2004; pp. 4829-4837; XP002581905; ISSN: 0022-2623.
Hutchinson, John et al.; Nonpeptide alphavbeta3 antagonists. 8. In vitro and in vivo evaluation of a potent alphavbeta3 antagonist for the prevention and treatment of osteoporosis; Journal of Medicinal Chemistry; vol. 46, No. 22; Oct. 23, 2003; pp. 4790- 4798; XP002581906; ISSN: 0022-2623, (only abstract was submitted).

* cited by examiner

*Primary Examiner* — D L Jones
(74) *Attorney, Agent, or Firm* — Gifford, Krass, Sprinkle, Anderson & Citkowski, P.C.

(57) ABSTRACT

The invention provides a family of agents that target integrins, which can be used as imaging agents and/or therapeutic agents. The agents can be used to image angiogenesis, inflammation or other physiological processes in a subject.

46 Claims, 8 Drawing Sheets

FIGURE 1
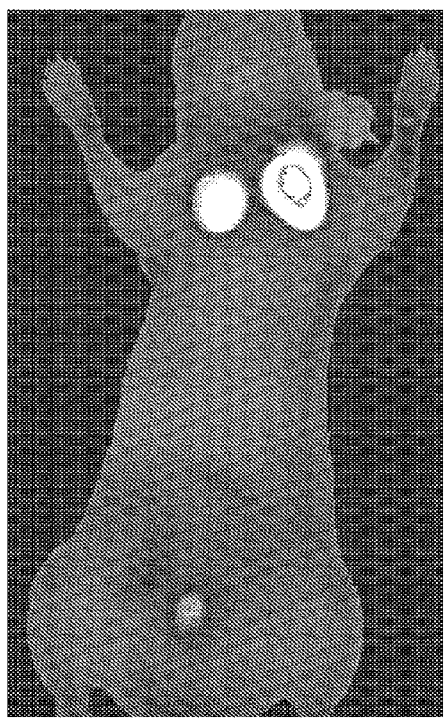 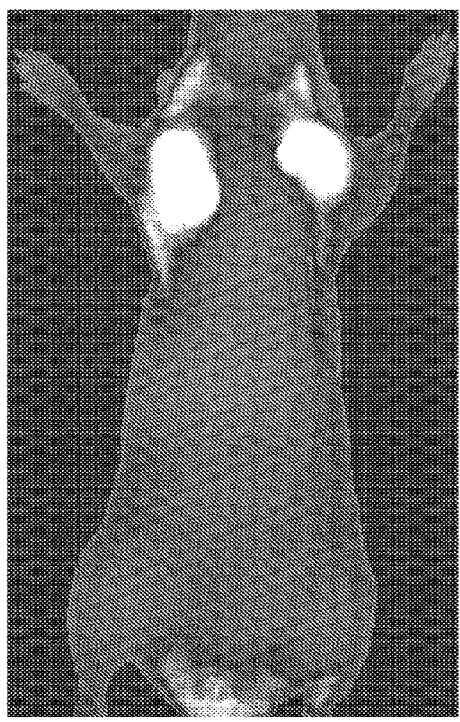
FIGURE 1A                FIGURE 1B

FIGURE 2A                    FIGURE 2B

FIGURE 3
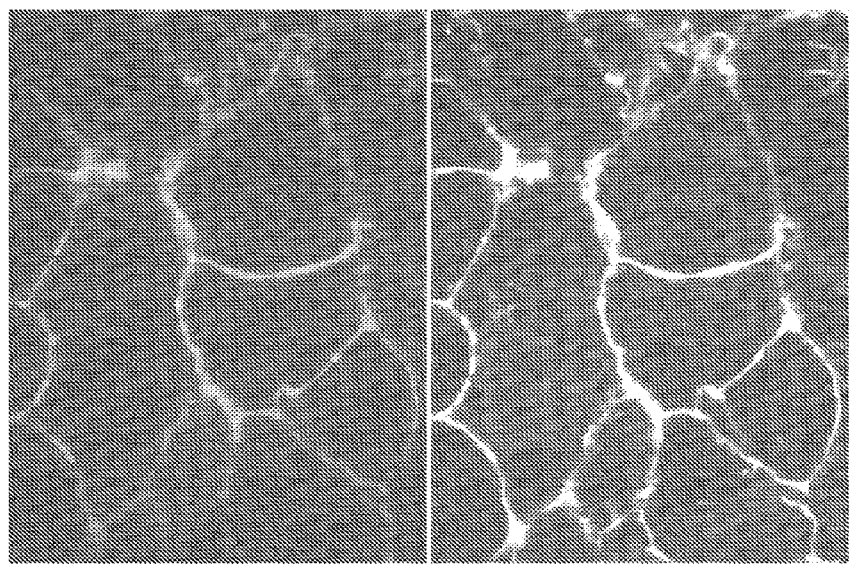
FIGURE 3A        FIGURE 3B
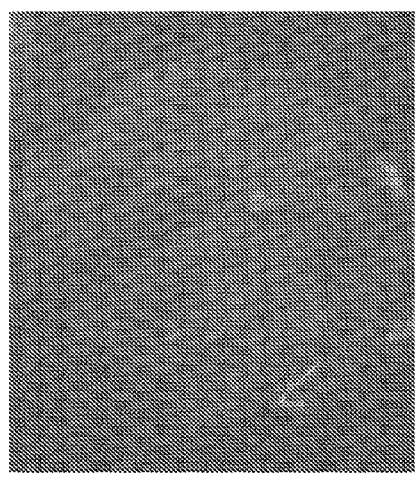  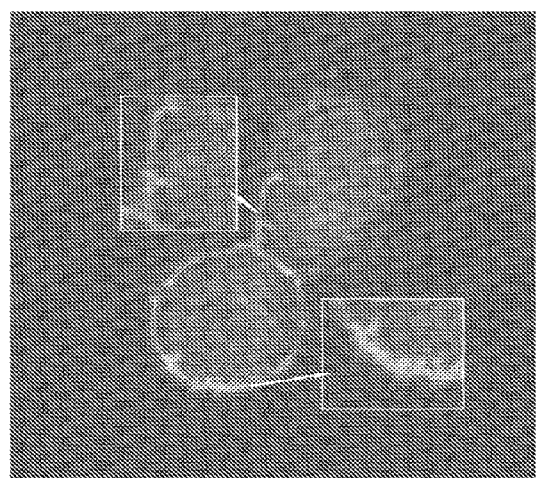
FIGURE 3C        FIGURE 3D FIGURE 4
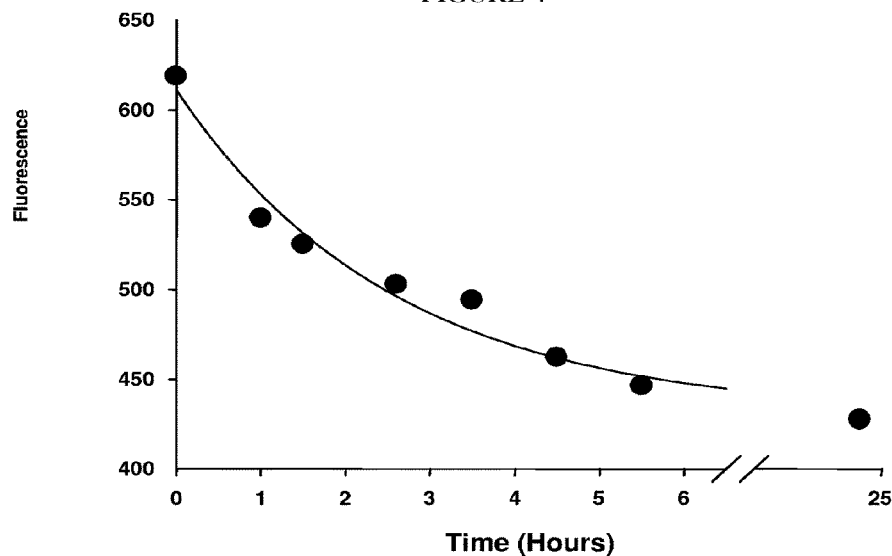
FIGURE 4A
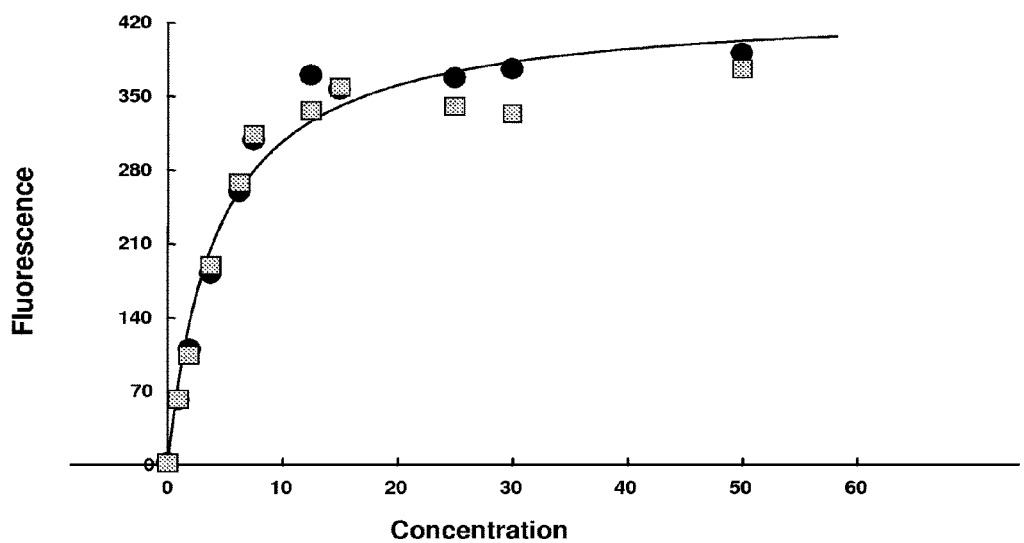
FIGURE 4B FIGURE 5
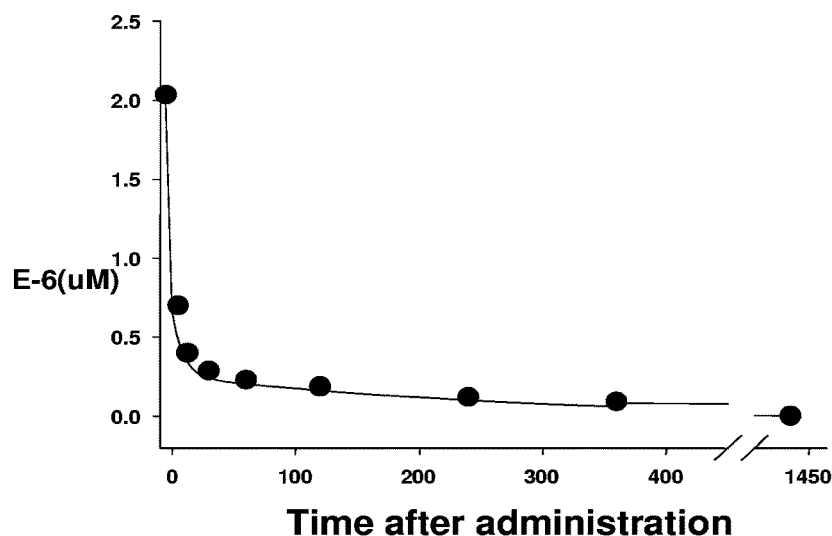
FIGURE 5A
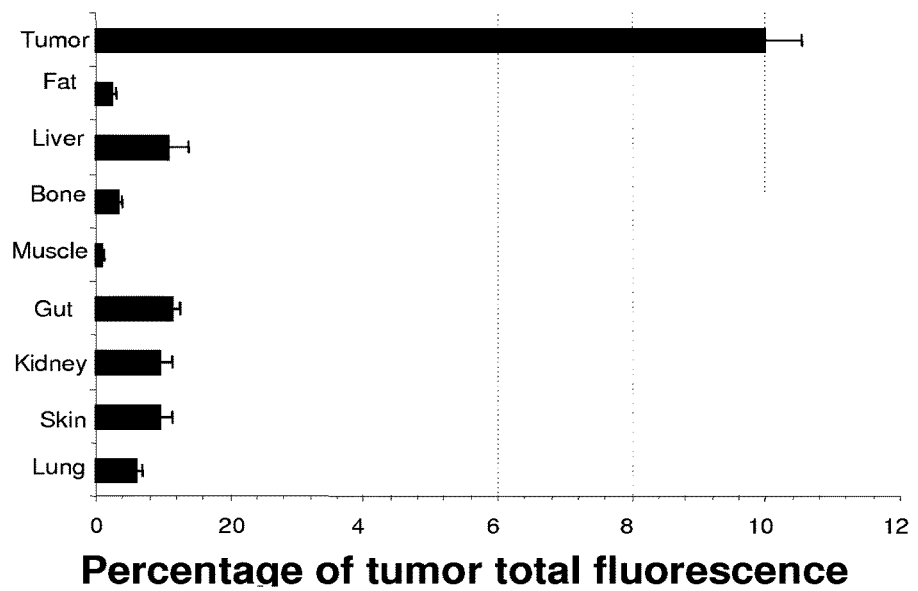
FIGURE 5B FIGURE 6
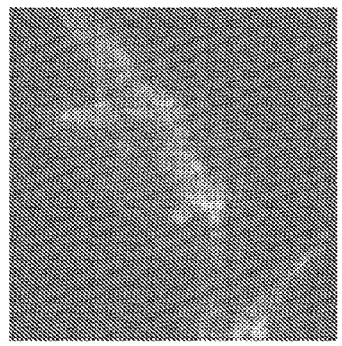
FIGURE 6A
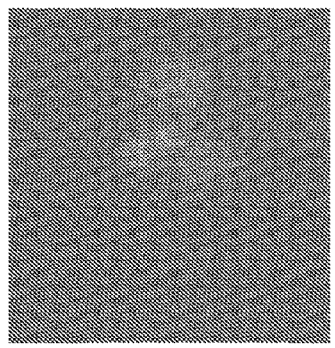
FIGURE 6B
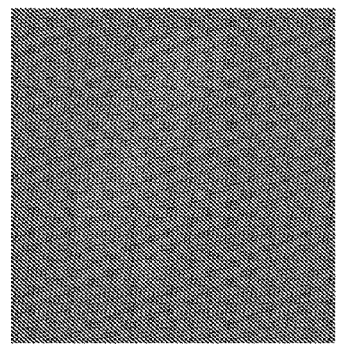
FIGURE 6C
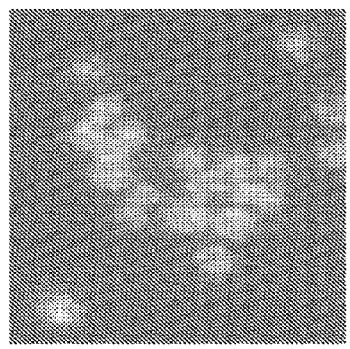
FIGURE 6D
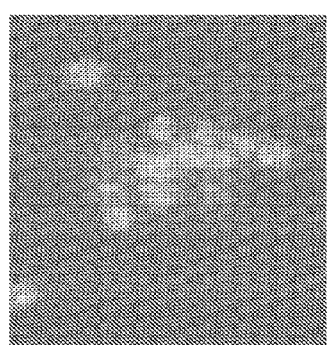
FIGURE 6E
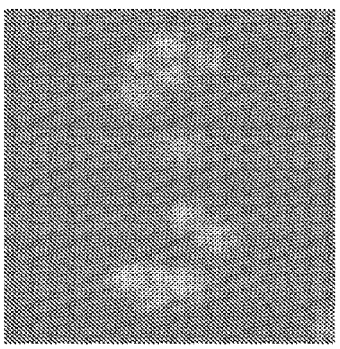
FIGURE 6F

INTEGRIN TARGETING AGENTS AND IN-VIVO AND IN-VITRO IMAGING METHODS USING THE SAME

CROSS-REFERENCE TO RELATED APPLICATIONS

This application is a national stage of International (PCT) Patent Application Ser. No. PCT/US2009/037114, filed Mar. 13, 2009, and published under PCT Article 21(2) in English, which claims the benefit of and priority to co-pending U.S. Provisional Patent Application No. 61/036,495, filed Mar. 14, 2008, the entire contents of each of which are incorporated by reference.

BACKGROUND

Current approaches for assessing molecular endpoints in certain diseases usually require tissue and blood sampling, surgery, and in the case of experimental animals, sacrifice at different time points. Despite improvements in noninvasive imaging, more sensitive and specific imaging agents and methods are urgently needed. Imaging techniques capable of visualizing specific molecular targets and/or entire pathways would significantly enhance our ability to diagnose and assess treatment efficacy of therapeutic interventions for many different disease states. Most current imaging techniques report primarily on anatomical or physiological information (e.g., magnetic resonance imaging (MRI), computed tomography (CT), and ultrasound). Newer modalities such as optical imaging and new molecular imaging probes have the potential to revolutionize the way disease is detected, treated, and monitored.

Molecular imaging is a new field in the imaging sciences that transcends the traditional boundaries of imaging structure or physiology and has the potential to revolutionize current research and clinical practices. The common paradigm for molecular imaging involves the use of a "molecular" probe or agent that selectively targets a particular gene, protein, receptor or a cellular function, with the absence, presence or level of the specific target being indicative of a particular disease state.

In particular, optical imaging offers several advantages that make it a powerful molecular imaging approach, both in the research and clinical settings. Specifically, optical imaging can be fast, safe, cost effective and highly sensitive. Scan times are on the order of seconds to minutes, there is no need for ionizing radiation, and the imaging systems can be relatively simple to use. In addition, optical probes can be designed as dynamic molecular imaging agents that may alter their reporting profiles in vivo to provide molecular and functional information in real time. In order to achieve maximum penetration and sensitivity in vivo, the choice for most optical imaging in biological systems is within the red and near-infrared (NIR) spectral region (600-900 nm), although other wavelengths in the visible region can also be used. In the NIR wavelength range, absorption by physiologically abundant absorbers such as hemoglobin or water is minimized.

Integrins are heterodimeric membrane receptors located on the cell surface that bind to the extracellular matrix (ECM). Upon ligand engagement outside of the cell, this class of adhesion receptors, through the single transmembrane helices of the dimeric subunits transmit, signals intracellularly, which can mediate a variety of biological consequences including cell growth, survival, differentiation, and apoptosis. Integrins regulate the cell cycle as well as cellular motility and morphology. In addition to binding to ECM, integrins also act as bridges connecting cells to other cells.

Structurally, integrins are heterodimeric proteins that comprise alpha ($\alpha$) and beta ($\beta$) chain subunits. Multiple forms of each subunit type exist (eighteen possible $\alpha$ chains and eight possible $\beta$ chains), allowing for great diversity in assembling heterodimeric integrins. Furthermore, splice variants of some subunits exist—allowing for even greater biological functionality and complexity. Integrins include $\alpha v\beta 1$, $\alpha v\beta 3$, $\alpha v\beta 5$, $\alpha v\beta 6$, $\alpha v\beta 8$, $\alpha 1\beta 1$, $\alpha 2\beta 1$, $\alpha 3\beta 1$, $\alpha 3\beta 6$, $\alpha 4\beta 1$, $\alpha 4\beta 7$, $\alpha 5\beta 1$, $\alpha 6\beta 4$, $\alpha 7\beta 1$, $\alpha 8\beta 1$, $\alpha 9\beta 1$, $\alpha 10\beta 1$, $\alpha L\beta 2$, $\alpha M\beta 2$, $\alpha X\beta 2$, $\alpha IIb\beta 3$, and more recently discovered $\alpha$ subunits pairing with $\beta 1$. Among these integrins, the following integrins $\alpha v$, $\alpha 5\beta 1$, $\alpha IIb\beta 3$ recognize the arginine-glycine-aspartic (RGD) sequence in proteins of the extracellular matrix (ECM). The alpha subunit associated integrins known as vitronectin receptors, $\alpha v\beta 3$, $\alpha v\beta 5$, and the fibronectin receptor $\alpha 5\beta 1$ regulate tumor cell migration and adhesion through this specific tri-amino acid moiety (Albelda et al., CANCER RES. 1990, 5:6757-6764; Gladson and Cheresh, J. CLIN. INVEST. 1991, 88:1924-1932; Lafrenie et al., EUR. J. CANCER, 1994, 30: 2151-2158).

Angiogenesis is the formation of new blood vessels, which is necessary for growth and development, tissue repair and tumor growth. Integrins $\alpha v\beta 3$, $\alpha v\beta 5$ and the fibronectin receptor are known to play key role in angiogenesis. For example the integrin $\alpha v\beta 3$ is highly expressed on activated endothelial cells during neovascularization, while weakly present in established blood vessels. This adhesion receptor $\alpha v\beta 3$ may be an attractive target for detecting the growth of any new vasculature.

SUMMARY OF THE INVENTION

The present invention provides agents that selectively target and bind certain integrins, in particular, $\alpha_v\beta_3$ integrin, and that can be used in a variety of in vitro and in vivo applications. The present invention also provides integrin targeting agents that can have fluorescent properties and/or magnetic properties (for example, paramagnetic or superparamagnetic properties) that can be used as MRI or multi-modality imaging agents (for example, optical imaging and magnetic resonance imaging). In addition, the present invention provides integrin targeting agents that, independently, and in combination, can comprise diagnostic and/or therapeutic radioactive metals, alone or in addition to other imaging agents, that can be used both as radiopharmaceuticals, nuclear imaging agents, or multi-modality imaging agents (for example, optical imaging and nuclear imaging).

The integrin targeting agents can be formulated into a pharmaceutical composition suitable for administration to a subject, for example, an animal and/or a human subject. The pharmaceutical composition can include one or more of the integrin agents and one or more stabilizers in a physiologically acceptable carrier.

In one aspect, the integrin targeting agent comprises: (a) an integrin targeting moiety (ITM) comprising an alkyl substituted tetrahydro-1,8-naphthyridine moiety, wherein the alkyl is substituted with an aryl or heteroaryl moiety; and (b) a reporter chemically linked, optionally through a linker (L) moiety, to the integrin targeting moiety. The alkyl can be substituted with a substituted or unsubstituted, monocyclic or bicyclic, heteroaryl moiety or aryl moiety.

The integrin targeting moiety, can include, for example, one to five integrin targeting moieties (for example, from two to five, three to five, or four to five integrin targeting moieties), each chemically linked to the imaging reporter. The agents can comprise a plurality of integrin targeting moieties each chemically linked to the imaging reporter.

The reporter can be, for example, a fluorophore reporter, a fluorochrome reporter, an optical reporter, a magnetic reporter, a radiolabel, an X-ray reporter, an ultrasound imaging reporter or a nanoparticle-based reporter or combination thereof. The integrin agent can further comprise a biological modifier chemically linked to the integrin targeting moiety, the reporter or to the optional linker.

In another aspect, the invention provides an integrin targeting agent represented by Formula I:

$$((ITM-L)_m-L_n-IR_q)-BM_g \qquad (I)$$

wherein
ITM represents an integrin targeting moiety comprising a substituted tetrahydro-1,8-naphthyridine moiety;
L, independently for each occurrence, represents a bond or a linker moiety;
IR represents an imaging reporter;
m represents an integer from 1 to 500, n represents an integer from 0 to 500, q represents an integer from 1 to 500, and g represents an integer from 0 to 500; and
BM represents a biological modifier.

It is understood that m can be an integer from 1 to 5; n can be an integer from 0 to 5; q can be an integer from 1 to 4 and/or g can be an integer from 0 to 3. In certain embodiments, n is 0 and g is 0. In certain embodiments, q is 1. In certain other embodiments, m can be 1 or 2.

In addition, the present invention provides methods for in vitro and in vivo imaging using the integrin targeting agents described herein. With respect to optical in vivo imaging, an exemplary method comprises (a) administering to a subject one or more of the foregoing integrin targeting agents of the invention, wherein the agents comprise one or more fluorchromes; (b) allowing the agent to distribute within the subject; (c) exposing the subject to light of a wavelength absorbable by at least one fluorochrome; and (d) detecting a signal emitted by the integrin agent. The signal emitted by the agent can be used to construct an image, for example, a tomographic image. Furthermore, it is understood that the foregoing steps can be repeated at predetermined intervals, which permit evaluation of the subject over time.

The integrin targeting agents can be used to measure angiogenesis (new blood vessel formation) or other physiological processes such as inflammation in a subject. One exemplary method comprises (a) administering one or more of the foregoing integrin targeting agents to a subject; and (b) detecting the presence of the agent(s) thereby to produce an image representative of new blood vessel formation in the subject.

In each of the foregoing methods, the subject can be a vertebrate, for example, a mammal, for example, a human. The subject also can be a non-vertebrate (for example, *C. elegans, drosophila*, or another model research organism) used in laboratory research.

In addition, the integrin targeting agents can be incorporated into a kit, for example, a kit with optional instructions for using the integrin targeting agents in in vivo or in vitro imaging methods. The kit optionally can include components that aid in the use of the integrin targeting agents, for example, buffers, and other formulating agents. Alternatively, the kit can include medical devices that aid in the administration and/or detection of the integrin targeting agents to a subject.

Other features and advantages of the invention will be apparent from the following figures, detailed description, and the claims.

BRIEF DESCRIPTION OF THE DRAWINGS

FIG. 1 depicts planar images of bilateral tumors at 24 hours after administration of exemplary compounds E-6 (FIG. 1A) and E-7 (FIG. 1B).

FIG. 3 depicts the binding of compound E-6 to HEK293-$\alpha_v\beta_3$ cells, wherein FIG. 3A shows images of HEK293-$\alpha_v\beta_3$ cells incubated with compound E-6 at 4° C. (FIG. 3A), with compound E-6 at 4° C. with cell mask and DAPI (FIG. 3B), with compound E-6 at 4° C. with parent compound DAPI (FIG. 3C), or with compound E-6 at 37° C. with parent compound DAPI (FIG. 3D)

FIG. 4 shows graphs depicting the dissociation (FIG. 4A) and equilibrium (FIG. 4B) binding constants respectively of exemplary compound E-6 with HEK293-$\alpha_v\beta_3$ cells.

FIG. 5 depicts the pharmacokinetic and biodistribution of compound E-6 in mice. FIG. 5A is a graph showing the concentration of compound E-6 in mice over time, and FIG. 5B is a bar chart showing fluorescence distribution among body tissues after administration of compound E-6.

FIG. 6 shows fluorescence images derived from endothelial cells (HUVEC) following incubation with compound E-6 (FIG. 6A), compound E-6 and parent compound (FIG. 6B), and with VivoTag s750 (FIG. 6C), and from tumor cells (A673) following incubation with compound E-6 (FIG. 6D), compound E-6 with parent compound (FIG. 6E), and with VivoTag s750 (FIG. 6F).

DETAILED DESCRIPTION

Figure 2:
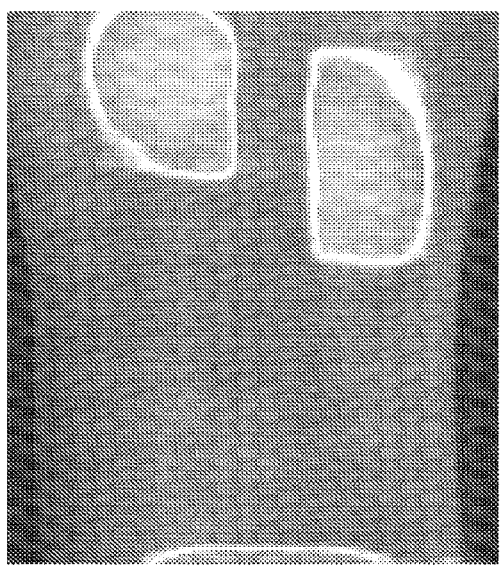
FIG. 2 depicts fluorescent molecular tomographic bilateral images of tumors 24 hours after administration of a ~2 nmol dose (FIG. 2A) and a ~4 nmol dose (FIG. 2B) of compound E-6.
Figure 2:
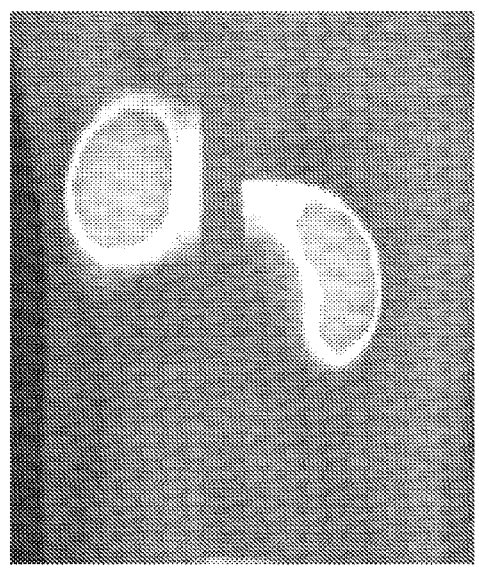

The invention is based, in part, upon the discovery that it is possible to produce integrin targeting agents that are stable and biocompatible, and that can be used in a variety of in vivo and in vitro assays and imaging applications, as well as in a variety of therapeutic applications.

The integrin targeting agents comprise at least one integrin targeting moiety (ITM) and a reporter, optionally an imaging reporter (IR), wherein one or more molecules of the ITM is chemically linked to one or more molecules of the reporter. Optionally, one or more linker (L) moieties can be used to chemically link the ITM to the reporter. In certain embodiments, the ITM is a molecule containing a substituted or an unsubstituted tetrahydronaphthyridine moiety, and the reporter is a fluorochrome molecule. In certain embodiments, the agents of the present invention bind to an integrin that is upregulated during angiogenesis.

The ITM can have an affinity for αv integrins; for example, αvβ5 and/or αvβ3 integrins. In one embodiment, the ITM has an affinity for αvβ3 integrin. As used herein, the term "integrin targeting moiety" or "ITM," is understood to mean a moiety that specifically binds with an integrin and/or prevents the binding of an integrin to its natural ligand. The binding between an ITM and an integrin may be covalent or non-covalent (for example, an electrostatic interaction, hydrophobic interaction, van der Waals interaction, hydrogen bonding, dipole interaction, etc.). For example, the binding between an ITM and an integrin is non-covalent.

The "imaging reporter" or "IR" can be any suitable molecule, chemical or substance that is used to provide the contrast or signal in imaging and that is detectable by imaging techniques. In certain embodiments, the imaging reporter comprises one or more fluorophores, photoluminescent nanoparticles, radioisotopes, superparamagnetic agents, X-ray contrast agents, and ultrasound agents. It is understood that the imaging reporter can also comprise a therapeutic reporter such as a porphyrin used in photodynamic therapy and/or radionuclide used in radiotherapy.

The term "affinity," as used herein, is understood to mean the ability of the integrin targeting agent to bind preferably to and/or be retained by an integrin.

As used herein, the term "chemically linked" is understood to mean connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions.

As used herein, the term "functionality" is understood to mean a reactive functional group that can be further modified or derivatized with another molecule. For example, the reactive functional group can be an amine, carboxylic acid, carboxylic ester, halogen, hydrazine, hydroxylamine, nitrile, isonitrile, isocyanate, isothiocyanate, thiol, maleimide, azide, alkyne, tetrazolyl, phosphonate, alkene, nitro, and nitroso.

As used herein, the term "biological modifier" or "BM" is understood to mean any moiety that can be used to alter the biological properties of the integrin agent, such as, without limitation, making the agent more water soluble or more dispersible in media for administration, increasing binding specificity, decreasing immunogenicity or toxicity, or modifying the pharmacokinetic profile compared to the non-BM modified integrin agents.

The term "alkyl" is art-recognized, and includes saturated aliphatic groups, including straight-chain alkyl groups, and branched-chain alkyl groups. Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromat-ics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

In certain embodiments, the integrin targeting agent comprises an integrin targeting moiety that includes an alkyl substituted tetrahydro-1,8-naphthyridine moiety, where the alkyl can be substituted with an aryl or heteroaryl moiety (e.g., a substituted or unsubstituted aryl), and an imaging reporter, for example, one or more fluorochromes, chemically linked, for example, by a bond or through a linker moiety to the integrin targeting moiety.

The integrin targeting agents can include one or more integrin targeting moieties each chemically linked to the imaging reporter and can include, for example, from 1 to 5 (for example, 1, 2, 3, 4, or 5) integrin targeting moieties. An exemplary integrin target agent is represented by Formula I:

$$((ITM-L)_m-L_n-IR_q)-BM_g \qquad (I)$$

wherein
ITM represents an integrin targeting moiety comprising a substituted tetrahydro-1,8-naphthyridine moiety, for example, an alkyl substituted tetrahydro-1,8-napthyridine moiety such as 7-alkyl-tetrahydro-1,8-napthyridine moiety;
L, independently for each occurrence, represents a bond or a linker moiety;
IR represents an imaging reporter;
m represents an integer between 1 to 500, n represents an integer between 0 to 500, q represents an integer between 1 to 500, and g represents an integer between 0 to 500;
and BM represents a biological modifier.

In certain embodiments, m can be an integer from 1 to 5, for example, 1, 2, 3, 4, or 5. Integer n, in some embodiments, can be an integer from 1 to 5, for example, 1, 2, 3, 4, or 5. In certain embodiments, the integer q can be an integer from 1 to 4, for example, 1, 2, 3 or 4. In certain embodiments, g can be an integer from 0 to 3, for example, 0, 1, 2 or 3. In certain embodiments, g is 0, n is 0, q is 1, and m is 1 or 2.

It is understood that the integrin targeting agents disclosed herein also include stereoisomeric forms thereof, or mixtures of stereoisomeric forms thereof, or pharmaceutically acceptable salt forms thereof.

In certain embodiments, the integrin targeting agent further comprises one or more biological modifiers, independently, chemically linked to the integrin targeting moiety, linker and/or imaging reporter or any combination thereof. Each of the features of the integrin targeting moieties, imaging reporters, linkers and biological modifiers are discussed in more detail below.

I. Integrin Targeting Moieties

Certain exemplary integrin targeting moieties useful in the practice of the invention are described in U.S. Pat. Nos. 6,048,861, 6,784,190, and 6,017,926; U.S. Patent Application No. US2002/0040030; European Application No. 1040111;

International Application Publication Nos. WO99/31061 and WO02/22616, all of which are incorporated herein by reference in their entirety.

When the integrin targeting moiety comprises a substituted tetrahydro-1,8-naphthyridine moiety, for example, an alkyl substituted tetrahydro-1,8-napthyridine moiety such as 7-alkyl-tetrahydro-1,8-naphthyridine moiety, the naphthyridine and/or the alkyl may optionally be substituted by one, two, or three substituents such as halo, hydroxyl, alkyl, alkoxy, and the like.

In certain embodiments, the integrin targeting moiety is represented by Formula II:

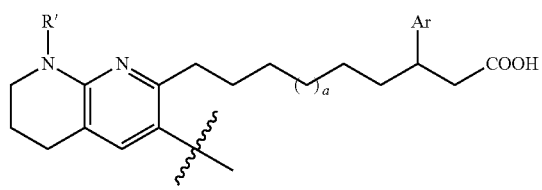

(II)

wherein Ar is an aromatic or partial aromatic moiety, and is an aryl or heteroaryl; R' is H or alkyl;

a represents an integer chosen from 0, 1, 2 or 3;

and salts thereof. In Formula II, and the other structures described herein, the bond crossed by the wavy line represents the bond that covalently couples the integrin targeting molecule to the remainder of the integrin targeting agent.

In certain embodiments, Ar is an monocyclic or bicyclic heteroaryl, or a monocyclic or bicyclic aryl, optionally substituted with 1, 2, or 3 moieties each independently selected from the group consisting of H, halo, alkoxy, alkyl, aryl, and heteroaryl. In other embodiments, R' is H.

In certain embodiments, the integrin targeting moiety is represented by Formula IIA:

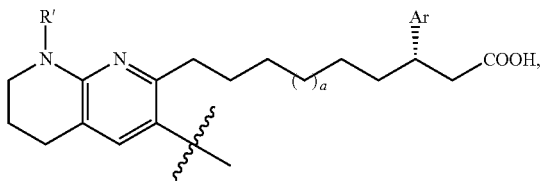

(IIA)

wherein R', Ar, and a are as denoted above in Formula II. Ar can be selected from the group consisting of:

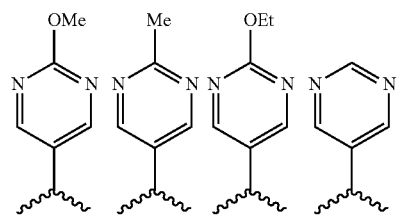

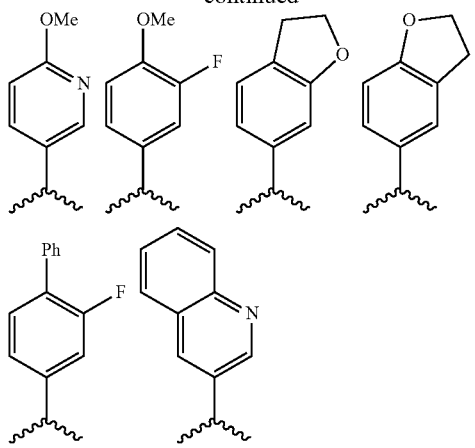

In certain embodiments, the integrin targeting moiety that can be used to create an integrin targeting agent is represented by Formula III:

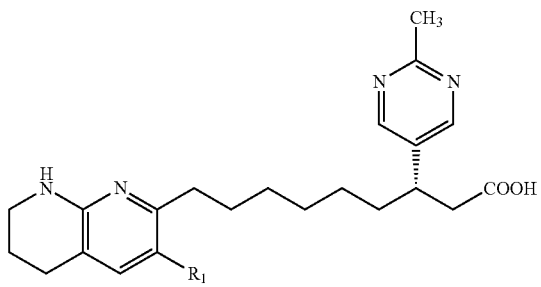

(III)

wherein $R_1$ provides a chemically functionality that can independently chemically link the integrin targeting moiety to a linker, imaging reporter or a biological modifier.

In certain embodiments, the integrin targeting moiety that can be used to create an integrin targeting agent is represented by Formula IV:

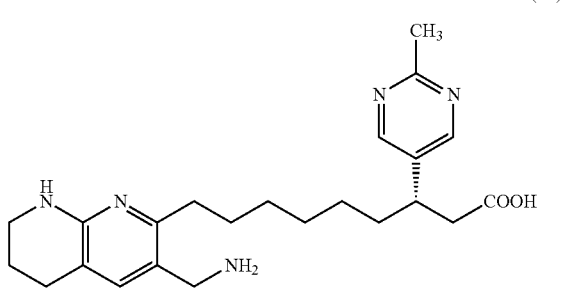

(IV)

wherein the $NH_2$, or NH—, for example, provides a functionality to independently, chemically link the integrin targeting moiety to a linker, imaging reporter or a biological modifier.

In certain embodiments, the integrin targeting moiety that can be used to create an integrin targeting agent is represented by Formula V:

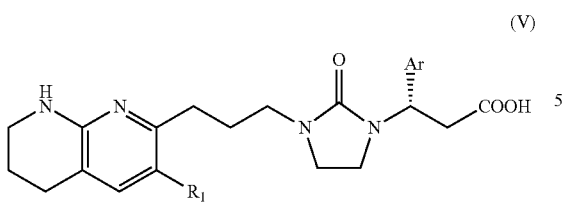

(V)

wherein, $R_1$ is defined above as in Formula III and Ar is as defined above in Formula II.

In certain embodiments, Ar of Formula V is selected from the group consisting of:

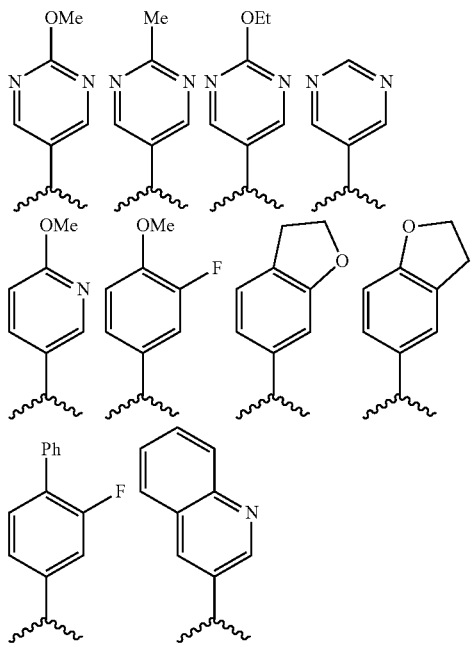

In certain embodiments, the integrin targeting moiety that can be used to create an integrin targeting agent is represented by Formula VI:

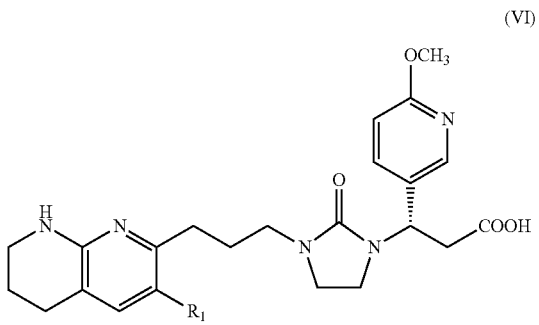

(VI)

wherein, $R_1$ provides a functionality to independently, chemically link the integrin targeting moiety to a linker, imaging reporter or a biological modifier.

In certain embodiments, the integrin targeting moiety that can be used to create an integrin targeting agent is represented by Formula VII:

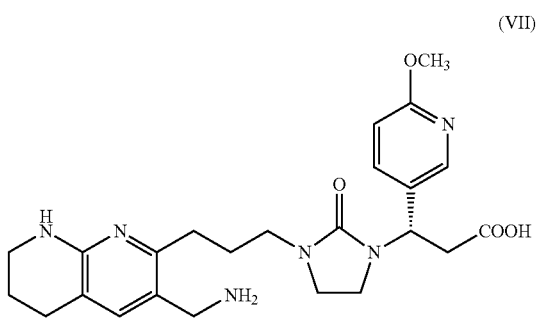 [SMILES: COc1ccc([C@H](CC(=O)O)N2CCN(CCCc3nc4c(cc3CN)CCCN4)C2=O)cn1]

(VII)

II. Imaging Reporters

It is understood that a variety of different imaging reporters, for example, fluorescent and non-fluorescent reporters can be used to produce an integrin targeting agent of the invention.

(a) Fluorescent Reporters

In certain embodiments, the imaging reporter is a fluorophore molecule. As used herein, the term "fluorophore," is understood to mean a fluorochrome, a fluorochrome quencher molecule, any organic or inorganic dye, metal chelate, or any fluorescent enzyme substrate, including protease activatable enzyme substrates.

In certain embodiments, the integrin imaging agents comprise a fluorochrome. In certain embodiments, the fluorochromes are far red and near infrared fluorochromes (NIRFs) with absorption and emission maximum between about 600 and about 1200 nm, more preferably between about 600 nm and about 900 nm. It is appreciated that the use of fluorochromes with excitation and emission wavelengths in other spectrums can also be employed in the compositions and methods of the present invention. Exemplary fluorochromes include but are not limited to a carbocyanine fluorochrome and an indocyanine fluorochrome.

Exemplary near infrared fluorochromes preferably have an extinction coefficient of at least 50,000 $M^{-1}cm^{-1}$ per fluorochrome molecule in aqueous medium. The near infrared fluorochromes preferably also have (1) high quantum yield (i.e., quantum yield greater than 5% in aqueous medium), (2) narrow excitation/emission spectrum, spectrally separated absorption and emission spectra (i.e., excitation and emission maxima separated by at least 15 nm), (3) high chemical and photostability, (4) nontoxicity, (5) good biocompatibility, biodegradability and excretability, and (6) commercial viability and scalable production for large quantities (i.e., gram and kilogram quantities) required for in vivo and human use.

Certain carbocyanine or polymethine fluorescent dyes can be used to produce the integrin agents of the invention and include, for example, those described in U.S. Pat. Nos. 6,747,159, 6,448,008, 6,136,612, 4,981,977, 5,268,486, 5,569,587, 5,569,766, 5,486,616, 5,627,027, 5,808,044, 5,877,310, 6,002,003, 6,004,536, 6,008,373, 6,043,025, 6,127,134, 6,130,094, and 6,133,445; also WO 97/40104, WO 99/51702, WO 01/21624, and EP 1 065 250 A1; and Tetrahedron Letters 41, 9185-88 (2000).

Various fluorochromes are commercially available and can be used to construct the integrin imaging agents of the invention. Exemplary fluorochromes include, for example, Cy5.5, Cy5 and Cy7 (GE Healthcare); AlexaFlour660, AlexaFlour680, AlexaFluor750, and AlexaFluor790 (Invitrogen); VivoTag680, VivoTag-S680, and VivoTag-S750 (VisEn Medical); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); and ADS780WS, ADS830WS, and ADS832WS (American Dye Source) and Kodak X-SIGHT 650, Kodak X-SIGHT 691, Kodak X-SIGHT 751 (Carestream Health).

Table 1 lists a number of exemplary fluorochromes useful in the practice of the invention together with their spectral properties.

TABLE 1

| Fluorochrome | $\epsilon_{max} M^{-1}cm^{-1}$ | Absorbance max (nm) |
|---|---|---|
| Cy5 | 250,000 | 649 |
| Cy5.5 | 250,000 | 675 |
| Cy7 | 250,000 | 743 |
| AlexaFlour660 | 132,000 | 663 |
| AlexaFlour680 | 184,000 | 679 |
| AlexaFlour750 | 280,000 | 749 |
| VivoTag680 (VT680) | 100,000 | 670 |
| VivoTag-S680 | 220,000 | 674 |
| VivoTag-S750 | 100,000 | 750 |
| Dy677 | 180,000 | 673 |
| Dy682 | 140,000 | 690 |
| Dy752 | 270,000 | 748 |
| Dy780 | 170,000 | 782 |
| DyLight547 | 150,000 | 557 |
| DyLight647 | 250,000 | 653 |
| IRDye800CW | 240,000 | 774 |
| IRDye800RS | 200,000 | 767 |
| IRDye700DX | 165,000 | 689 |
| ADS780WS | 170,000 | 782 |
| ADS830WS | 240,000 | 819 |
| ADS832WS | 190,000 | 824 |

In one embodiment, an exemplary fluorochrome is represented by Formula VIII:

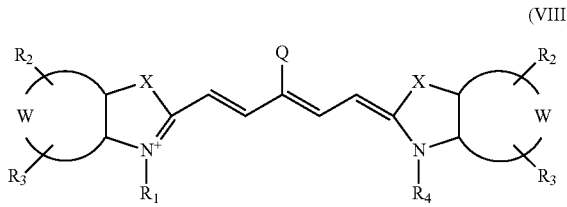

(VIII)

or a salt thereof, wherein:

X is independently selected from the group consisting of $C(CH_2Y_1)(CH_2Y_2)$, O, S, and Se;

$Y_1$ and $Y_2$ are independently selected from the group consisting of H, aliphatic group and a $C_1$-$C_{20}$ aliphatic group substituted with —OR*, N(R*)$_2$ or —SR*;

W represents a benzo-condensed, a naphtho-condensed or a pyrido-condensed ring;

$R_1$ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6;

$R_4$ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6;

$R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is selected from a group consisting of a heteroaryl ring substituted with a carboxyl group or 6-membered heteroaryl ring substituted with a carbonyl group.

Q is selected from a group consisting of (i) a carboxyl functionalized heterocyclic ring, (ii) a carboxyl functionalized nitrogen containing heterocyclic ring, (iii) a carboxyl functionalized nitrogen containing 6-membered heterocyclic ring, such as pyridine, pyrimidone, pyrazine, and pyridazine, (iv) a carboxyl functionalized nitrogen containing 6-membered heterocyclic ring, such as pyridine, (v) a carbonyl functionalized nitrogen containing 6-membered heterocyclic ring, such as pyridine, (vi) an isonicotinic acid, nicotinic acid and picolinic acid, and a group selected from:

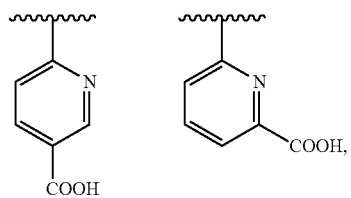

wherein, the carboxyl group is also in the form of an ester, an activated ester or carbonyl halide that is capable of reacting with nucleophiles, and can be, for example, a CO-Obenzotriazolyl, CO—ON-hydroxysuccinimidyl, CO-Otetrafluorophenyl, CO-Opentafluorophenyl, CO-Oimidazole, and CO-Op-nitrophenyl.

In another embodiment, an exemplary fluorochrome is represented by Formula IX:

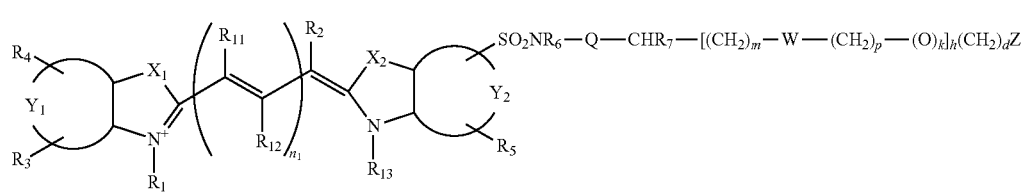

(IX)

or a salt thereof, wherein:

$X_1$ and $X_2$ are independently selected from the group consisting of $C(CH_2K_1)(CH_2K_2)$, O, S and Se;

$K_1$ and $K_2$ are independently selected from the group consisting of H, a $C_1$-$C_{20}$ aliphatic group and a $C_1$-$C_{20}$ aliphatic group substituted with —OR*, N(R*)$_2$ or —SR*; or $K_1$ and $K_2$ together are part of a substituted or unsubstituted carbocyclic, or heterocyclic ring;

$Y_1$ and $Y_2$ are each independently a benzo-condensed ring, a naphtha-condensed ring or a pyrido-condensed ring;

$n_1$ is 1, 2, or 3;

$R_2$, $R_{11}$ and $R_{12}$ are independently H, F, Br, $C_1$, $C_1$-$C_6$ alkyl, $C_1$-$C_6$ alkoxy, aryloxy, a nitrogen-containing heterocyclic ring, a nitrogen-containing heteroaromatic ring, a sulfonate, an iminium ion, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*;

$R_1$ and $R_{13}$ are $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, N(R*)$_2$ or SR*, when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or $R_6$ is H, when Q is a carbonyl; and $R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*; or $R_6$ and $R_7$, taken together form a 4-, 5-, 6- or 7-membered heterocyclic or non-aromatic heterocyclic ring optionally substituted with halogen, OR*, N(R*)$_2$ or SR*; or $NR_6$, Q and $CHR_7$ together form a substituted or unsubstituted or heterocyclic or non-aromatic heterocyclic ring system wherein the rings contain 1 or 2 heteroatoms, wherein rings are optionally substituted with —OR*, N(R*)$_2$ or —SR*; and W is absent or is a group selected from the group consisting of —SO$_2$NR$_6$-Q-CHR$_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles; and each R* is independently —H or C1-20 alkyl.

Exemplary fluorophores that can be used in the synthesis of the integrin agents of the invention include, for example, those listed in Table 2.

TABLE 2

| No. | Fluorophore |
|-----|-------------|
| 1 | (Formula A1) |
| 2 | (Formula B1) |

TABLE 2-continued

| No. | Fluorophore |
| --- | --- |
| 3 | (Formula C1) |
| 4 | (Formula D1) |
| 5 | (Formula E1) |

TABLE 2-continued

| No. | Fluorophore |
|---|---|
| 6 | |
| 7 | |
| 8 | |
| 9 | |
| 10 | |

TABLE 2-continued

| No. | Fluorophore |
| --- | --- |
| 11 | |
| 12 | |
| 13 | |
| 14 | |

TABLE 2-continued

| No. | Fluorophore |
|---|---|
| 15 | |
| 16 | |

In certain embodiments, one or more fluorochrome molecules can be chemically linked to the integrin targeting moiety to produce the fluorescent integrin targeting agents.

In the case where the imaging reporter is a fluorochrome molecule, the extinction coefficient of the integrin agents can be calculated as the ratio of the absorbance of dye at its absorption maxima (for example at ~670 nm for VivoTag 680) in a 1 cm path length cell to the concentration of particles using the formula $\epsilon = A/cl$, where A is absorbance, c is molar concentration and l is path length in cm.

It is understood that integrin imaging agent can be linked to nanoparticles (for example, silicon containing nanoparticles) to produce fluorescent or luminescent nanoparticles. Aggregates of crystalline silicon (as multiple or single crystals of silicon), porous silicon, or amorphous silicon, or a combination of these forms, can form the nanoparticle. Preferred fluorescent silicon nanoparticles have a diameter between about 0.5 nm to about 25 nm, more preferably between about 2 nm and about 10 nm. The size of nanoparticles can be determined by laser light scattering or by atomic force microscopy or other suitable techniques.

Fluorescent silicon nanoparticles may have excitation and emission spectra from 200 nm to 2000 nm, however, preferred fluorescent silicon nanoparticles have excitation and emission maximum from between about 400 nm to about 1200 nm (and preferably 500 nm-900 nm, for example, 500 nm-600 nm, 600 nm-700 nm, 700 nm-800 nm, or 800 nm-900 nm). Preferred fluorescent silicon nanoparticles also have extinction coefficients of at least 50,000 $M^{-1}cm^{-1}$ in aqueous medium. Although fluorescent silicon nanoparticles that have excitation and emission maximum between 400 nm and 1200 nm are preferred, it is appreciated that the use of fluorescent silicon nanoparticles with excitation and emission wavelengths in other spectrums can also be employed in the compositions and methods of the present invention. For example, in certain embodiments, the particles may have excitation wavelengths in the range of 300-350 nm, and emission wavelengths in the range of 400-450 nm.

Fluorescent silicon nanoparticles may also have the following properties: (1) high quantum yield (i.e., quantum yield greater than 5% in aqueous medium), (2) narrow emission spectrum (i.e., less than 75 nm; more preferably less than 50 nm), (3) spectrally separated absorption and emission spectra (i.e., separated by more than 20 nm; more preferably by more than 50 nm), (3) have high chemical stability and photostability (i.e., retain luminescent properties after exposure to light), (4) are biocompatible or can be made more biocompatible; (5) are non toxic or minimally toxic to cells or subjects at doses used for imaging protocols (as measured for example, by $LD_{50}$ or irritation studies, or other similar methods known in the art) and/or (6) have commercial viability and scalable production for large quantities (i.e., gram and kilogram quantities) required for in vivo and human use.

Other exemplary fluorophores include metal oxide nanoparticles that are fluorescent and can be used in a variety of in vitro and in vivo applications. In one embodiment, the integrin targeting moieties are conjugated to fluorescent metal oxide nanoparticles with one or more of the following features: (1) a polymer coating suitable for attaching a plurality of fluorochromes thereby achieving large extinction coefficients (in excess of 1,000,000 $M^{-1}cm^{-1}$), (2) a non-crosslinked polymer coating suitable for attaching from about 10 to about 300 fluorochromes per particle, (3) a polymer coating suitable for attaching a plurality of fluorochromes in a manner that does not significantly compromise the quantum yield of the fluorochromes (e.g., the nanoparticles retain at least 50% of the fluorescent signal that is created by substantially the same number of free fluorochromes when tested under the same conditions), and (4) a polymer coating that is amenable to efficient chemical linking of biomolecules with retention of their biological properties to yield molecular imaging agents. The fluorescent metal oxide nanoparticles are highly stable molecular imaging agents in vitro, both before and after chemical linkage to other elements of the integrin targeting agent, but yet are labile and/or degradable in vivo.

The integrin targeting moiety can be linked to fluorescent quantum dots such as amine T2 MP EviTags (Evident Technologies) or Qdot Nanocrystals (Invitrogen). In general, fluorescent quantum dots are nanocrystals containing several atoms of a semiconductor material (including but not limited to those containing cadmium and selenium, sulfide, or tellurium; zinc sulfide, indium-antimony, lead selenide, gallium arsenide, and silica or ormosil, which have been coated with zinc sulfide to improve the properties of these fluorescent agents.

Furthermore, the integrin targeting moiety can be conjugated to molecules capable of eliciting photodynamic therapy. These include, but are not limited to, Photofrin, Lutrin, Antrin, aminolevulinic acid, hypericin, benzoporphyrin derivative, and select porphyrins.

In certain embodiments, one or more different fluorophore molecules can be covalently linked to a cleavable (for example, an enzymatically cleavable) oligopeptide, or alternatively, two substantially similar fluorophores can be covalently linked to the oligopeptide, at fluorescence-quenching permissive locations separated by a cleavage site, for example, a proteolytic cleavage site, to produce the imaging agents of the invention.

In certain embodiments, a quencher is used to quench the fluorescent signal from the fluorophore covalently linked to the oligopeptide. For example, an agent can be designed such that the quencher quenches the fluorescence of the fluorophore of the imaging agent when the agent is in an unactivated state, so that the imaging agent exhibits little or no signal until it is activated. It is understood that the quencher can be a non-fluorescent agent, which when suitably located relative to a fluorophore (i.e., at a fluorescence-quenching permissive location) is capable of quenching the emission signal from the fluorophore. It is understood that certain of the foregoing fluorophores can act to quench the fluorescent signal of another spaced apart fluorophore, when the two fluorophores are positioned at fluorescence-quenching interaction permissive locations.

A number of quenchers are available and known to those skilled in the art including, but not limited to 4-{[4-(dimethylamino)-phenyl]-azo}-benzoic acid (DABCYL), QSY®-7 (9-[2-[(4-carboxy-1-piperidinyl)sulfonyl]phenyl]-3,6-bis (methylphenylamino)-xanthylium chloride) (Molecular Probes, Inc., OR), QSY®-33 (Molecular Probes, Inc., OR), ATTO612Q, ATTO580Q (ATTO-TEC, Germany); Black Hole Quenchers® (Bioresearch Technologies, Novato, Calif.), QXL™680 Acid (AnaSpec, San Jose Calif.), and fluorescence fluorophores such as Cy5 and Cy5.5 (e.g., 2-[5-[3-[6-[(2,5-dioxo-1-pyrrolidinyl)oxy]-6-oxohexyl]-1,3-dihydro-1,1-dimethyl-6,8-disulfo-2H-benz[e]indol-2-ylidene]-1,3-pentadienyl]-3-ethyl-1,1-dimethyl-6,8-disulfo-1H-benz[e]indolium, inner salt) (Schobel, *Bioconjugate* 10:1107, 1999). Other quenching strategies can be used, for example, using various solvents to quench fluorescence of the agents.

Exemplary fluorophores that can quench the emission of other fluorophores are represented in Table 3.

TABLE 3

| No. | Quencher |
|---|---|
| 1 | 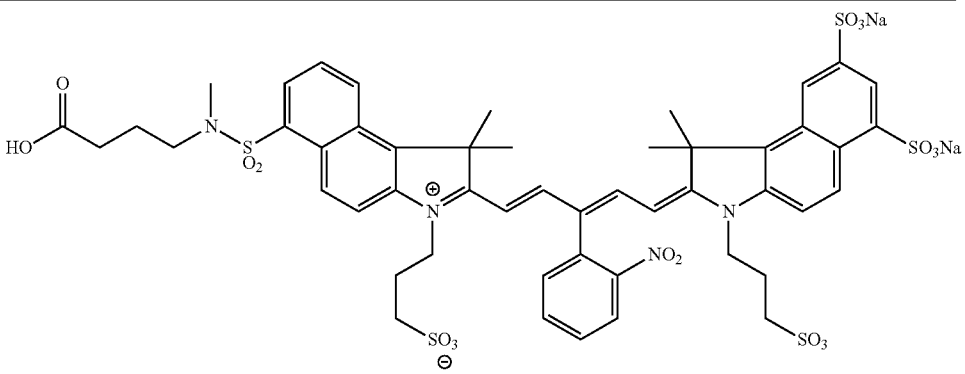 |
| 2 | 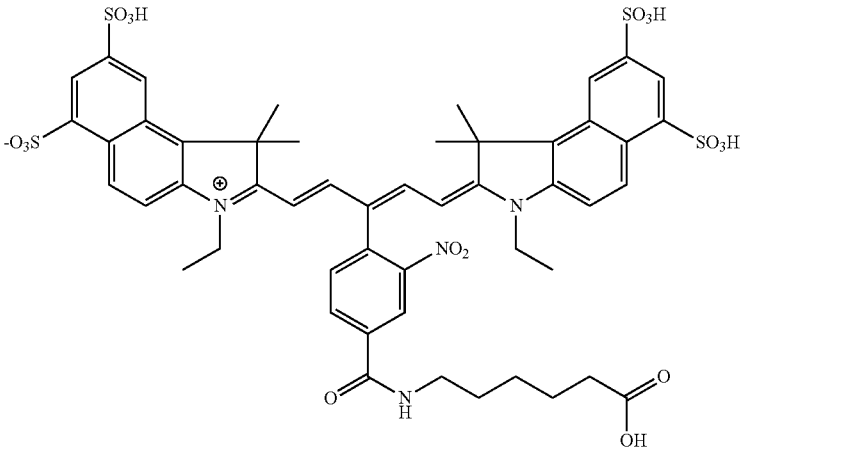 |

In such embodiments, the two fluorophores or the fluorophore and the quencher are located within the intact imaging agent at fluorescent-quenching interaction permissive positions. In other words, a first fluorophore is located close enough in the intact imaging agent to a second fluorophore (or quencher) to permit them to interact photochemically with one another so that the second fluorophore (or quencher) quenches the signal from the first fluorophore. In the case of the imaging agents with two fluorophores, one fluorophore preferably quenches the other fluorophore. For principles of quenching, see U.S. Pat. No. 6,592,847.

(b) Non-Fluorescent Reporters

The term "non-fluorescent reporter," as used herein, refers to a chemical moiety that is not fluorescent but which can be used to provide the contrast or signal in imaging and is detectable by a non-fluorescent imaging technique. In certain embodiments, other non-fluorescent reporters can be chemically linked with the imaging moieties, or can be administered to a subject simultaneously or sequentially with the imaging agents of the invention. Such reporters can include photoluminescent nanoparticles, radioisotopes, superparamagnetic agents, X-ray contrast agents, and ultrasound agents. A reporter may also comprise therapeutic reporters such as porphyrins, Photofrin®, Lutrin®, Antrin®, aminolevulinic acid, hypericin, benzoporphryrin derivatives used in photodynamic therapy, and radionuclides used for radiotherapy.

(i) Radioactive Reporters

The agents can include one or more radioactive labels. Radioisotopic forms of metals such as copper, gallium, indium, technetium, yttrium, and lutetium can be chemically linked to the metallic imaging agents and can be used for nuclear imaging or therapeutic applications. Exemplary radioactive labels include, without limitation, $^{99m}$Tc, $^{111}$In, $^{64}$Cu, $^{67}$Ga, $^{186}$Re, $^{188}$Re, $^{153}$Sm, $^{177}$Lu, and $^{67}$Cu.

Other exemplary labels include, for example, $^{123}$I, $^{124}$I, $^{125}$I, $^{11}$C, $^{13}$N, $^{15}$O, and $^{18}$F. Other exemplary labels can be therapeutic radiopharmaceuticals including, for example, $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir.

Chelators or bonding moieties for diagnostic and therapeutic radiopharmaceuticals are also contemplated and can be chemically associated with the imaging agents. Exemplary chelators can be selected to form stable complexes with radioisotopes that have imageable gamma ray or positron emissions, such as $^{99m}$Tc, $^{111}$In, $^{64}$Cu, and $^{67}$Ga. Exemplary chelators include diaminedithiols, monoamine-monoamidedithiols, triamide-monothiols, monoamine-diamide-monothiols, diaminedioximes, and hydrazines. Chelators generally are tetradentate with donor atoms selected from nitrogen, oxygen and sulfur, and may include for example, cyclic and acyclic polyaminocarboxylates such as diethylenetriaminepentaacetic acid (DTPA), 1,4,7,10-tetraazacyclododecane-1,4,7,10-tetraacetic acid (DOTA), (DO3A), 2-benzyl-DOTA, alpha-(2-phenethyl)1,4,7,10-tetraazcyclododecane-1-acetic-4,7,10-tris(methylacetic) acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

(ii) Magnetic Reporters

Other exemplary reporters can include a chelating agent for magnetic resonance imaging agents. Such chelators can include, for example, polyamine-polycarboxylate chelators or iminoacetic acid chelators that can be chemically linked to the agents.

Chelators for magnetic resonance imaging agents can be selected to form stable complexes with paramagnetic metal ions, such as Gd(III), Dy(III), Fe(III), and Mn(II), are selected from cyclic and acyclic polyaminocarboxylates such as DTPA, DOTA, DO3A, 2-benzyl-DOTA, alpha-(2-phenethyl) 1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyeaminomethyl)-4'-(3-amino-4-methoxyphenyl)-2,2':6',2"-terpyridine.

In one embodiment, the integrin agents are conjugated to superparamagnetic metal oxide nanoparticles that are either (a) non-fluorescent or (b) are fluorescent and can be used in a variety of in vitro and in vivo applications. Fluorescent metal oxide nanoparticles that also have magnetic properties can be used for MRI, thus providing a multi-modality imaging agent.

In certain embodiments, the imaging agents can include a fluorescent and/or non-fluorescent superparamagenetic metal oxide nanoparticle with one or more of the following features: (1) a polymer coating suitable for attaching a plurality of agents (2) a non-crosslinked polymer coating suitable for attaching from about 10 to about 300 agents per particle, and (3) a polymer coating that is amenable to efficient chemical linking of the agents with retention of their biological properties to yield molecular imaging agents. The agent modified metal oxide nanoparticle can be a highly stable molecular imaging agent in vitro, both before and after chemical linking of the agents, but yet are labile and/or degradable in vivo.

The integrin agent conjugated metal oxide nanoparticles can be formulated into a pharmaceutical composition suitable for administration to a subject, for example, an animal and/or a human subject.

(iii) Ultrasound Reporters

For ultrasound imaging, the imaging reporter can include gas-filled bubbles such as Levovist, Albunex, or Echovist, or particles or metal chelates where the metal ions have atomic numbers 21-29, 42, 44 or 57-83. Examples of such compounds are described in Tyler et al., ULTRASONIC IMAGING, 3, pp. 323-29 (1981) and Swanson, "Enhancement Agents for Ultrasound: Fundamentals," PHARMACEUTICALS IN MEDICAL IMAGING, pp. 682-87 (1990).

(iv) X-Ray Reporters

Exemplary reporters can comprise iodinated organic molecules or chelates of heavy metal ions of atomic numbers 57 to 83. Examples of such compounds are described in Sovak, ed., "Radiocontrast Agents," SPRINGER-VERLAG, pp. 23-125 (1984) and U.S. Pat. No. 4,647,447.

III. Linkers

Linker or spacer moieties can be used to chemically link one or more imaging reporters and/or integrin targeting moieties and/or biological modifiers to produce the integrin agents of the invention. Useful linker moieties include both natural and non-natural amino acids and nucleic acids, peptides, as well as synthetic linker molecules such as aminoethyl maleimide. When the linker is a peptide, the peptide optionally may include proteolytic cleavage site that can be cleaved with a variety of agents, for example, an enzyme.

It is understood that there is no particular structural, size or content limitation for a given linker. Linkers can include, for example, a variety of functional groups such as maleimide, dithiopyridyl, thiol, azide, alkene, or alkyne that permit the assembly of molecules of diverse architecture.

Linkers can be homofunctional linkers or heterofunctional linkers. For example, amine ($NH_2$)-functionalized moieties can be reacted with bifunctional cross-linkers designed to react with amino groups. Particularly useful conjugation reagents that can facilitate formation of a linker or facilitate covalent linkage between, for example, a fluorophore, and an enzymatically cleavable oligopeptide can include a N-hydroxysuccinimide (NHS) ester and/or a maleimide. The NHS ester can react with the amine group of, for example, a peptide or fluorophore. The maleimide can react with the sulfhydryl group of another molecule. Other particularly useful linker moieties are bifunctional crosslinkers such as N-succinimidyl 3-(2-pyridyldithio)propionate (SPDP), long chain-SPDP, maleimidobenzoic acid-N-hydroxysuccinimide ester (MBS), succinimidyl trans-4-(maleimidylmethyl)cyclohexane-1-carboxylate (SMCC), succinimidyl iodoacetate (SIA).

In certain embodiments a linker, if present, may be a derivative of a diamine. A diamine moiety or derivative can provide a linker arm of varying lengths and chemistries for chemically linking molecules by derivatizing, optionally, with carboxylic acids. Non-limiting examples of diamines include ethylenediamine (EDA), propylenediamine, spermidine, spermine, hexanediamine, and diamine-amino acids, such as homolysine, lysine, ornithine, diaminobutyric acid and diaminopropionic acid. In other embodiments, moieties of an imaging agent can be chemically linked to a dicarboxylic acid, for example, succinic acid, glutaric acid, suberic acid, or adipic acid. In one embodiment, the linker is aminoethylmaleimide.

In certain embodiments, a linker can be formed from an azide moiety that can react with substituted alkynes in an azide-acetylene Huisgen [3+2] cycloaddition. In certain embodiments, the azide or alkyne linker can link a polyethyleneglycol (PEG) moiety to, for example, an enzymatically cleavable oligopeptide. Other contemplated linkers include propargylglycine, pentanoyl, pentynoic acid, propargylic acid, and/or propargylamine moieties.

In certain embodiments, the imaging reporters are directly chemically linked to the integrin targeting moiety using reactive NHS esters groups on the imaging reporter which react with the amine group of the amino-functionalized imaging targeting moiety. In certain other embodiments, carboxylic acid groups on the imaging reporter can be activated in situ by activating agents known in the art, such as 2-(1H-benzotriazole-1-yl)-1,1,3,3,-tetramethyluronium hexafluorophosphate (HBTU), 1-ethyl-3-(3'-dimethylaminopropyl)-carbodiimide hydrochloride (EDC), N,N'-dicyclohexylcarbodiimide (DCC), N,N'-disuccinimidyl carbonate (DSC). In other embodiments, imaging reporters containing a sulfhydryl or thiol group, can be chemically linked to the imaging targeting moiety via a bifunctional cross-linker that has a second moiety that can react with a sulfhydryl (thiol) group. Such crosslinking agents include, for example and as described above, SPDP, long chain-SPDP, SIA, MBS, SMCC, and others that are well known in the art.

Useful linker moieties include both natural and non-natural amino acids, oligopeptides, for example, linear or cyclic oligopeptides, and nucleic acids. The linker can be a peptide or peptide moiety, which optionally includes a proteolytic or non-proteolytic cleavage site, such as an ester linkage, that can be cleaved due to pH changes at the site of interest.

As used herein, the term "enzymatically cleavable oligopeptide," is understood to mean, a peptide comprising two or more amino acids that are linked by means of a enzymatically cleavable peptide bond. Also included are moieties that include a pseudopeptide or peptidomimetic. Examples of cleavable peptide substrates can be found in U.S. Pat. No. 7,439,319.

The term "amino acid," as used herein, is understood to mean an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Natural amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Other amino acids include, but not limited to, arginosuccinic acid, citrulline, cysteine sulfinic acid, 3,4-dihydroxyphenylalanine, homocysteine, homoserine, ornithine, carnitine, selenocysteine, selenomethionine, 3-monoiodotyrosine, 3,5-diiodotryosine, 3,5,5'-triiodothyronine, and 3,3',5,5'-tetraiodothyronine.

Modified or unusual amino acids that can be used in the practice of the invention include, but are not limited to, D-amino acids, hydroxylysine, dehydroalanine, pyrrolysine, 2-aminoisobutyric acid, gamma aminobutyric acid, 5-hydroxytryptophan, S-adenosyl methionine, S-adenosyl homocysteine, 4-hydroxyproline, an N-Cbz-protected amino acid, 2,4-diaminobutyric acid, homoarginine, norleucine, N-methylaminobutyric acid, naphthylalanine, phenylglycine, .beta.-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

As used herein, a "pseudopeptide" or "peptidomimetic," is a compound which mimics the structure of an amino acid residue or a peptide, for example, by using linking groups other than via amide linkages (pseudopeptide bonds) and/or by using non-amino acid substituents and/or a modified amino acid residue. A "pseudopeptide residue" means that portion of a pseudopeptide or peptidomimetic that is present in a peptide. The term "pseudopeptide bond" includes peptide bond isosteres that may be used in place of or as substitutes for the normal amide linkage. The substitute or amide "equivalent" linkages are formed from combinations of atoms not normally found in peptides or proteins which mimic the spatial requirements of the amide bond and which should stabilize the molecule to enzymatic degradation. The following conventional three-letter amino acid abbreviations are used herein: Ala=alanine; Aca=aminocaproic acid, Ahx=6-aminohexanoic acid, Arg=arginine; Asn=asparagines; Asp=aspartic acid; Cha=cyclohexylalanine; Cit=citrulline; Cys=cysteine; Dap=diaminopropionic acid; Gln=glutamine; Glu=glutamic acid; Gly=glycine; His=histidine; Ile=isoleucine; Leu=leucine; Lys=lysine; Met=methionine; Nal=naphthylalanine; Nle=norleucine; Orn=ornithine; Phe=phenylalanine; Phg=phenylglycine; Pro=praline; Sar=sarcosine; Ser=serine; Thi=Thienylalanine; Thr=threonine; Trp=tryptophan; Tyr=tyrosine; and Val=valine. Use of the prefix D- indicates the D-isomer of that amino acid; for example D-lysine is represented as D-Lys.

The peptides can be synthesized using either solution phase chemistry or solid phase chemistry or a combination of both (Albericio, Curr. Opinion. Cell Biol., 8, 211-221 (2004), M. Bodansky, Peptide Chemistry: A Practical Textbook, Springer-Verlag; N. L. Benoiton, Chemistry of Peptide Synthesis, 2005, CRC Press).

Selective or orthogonal amine protecting groups may be required to prepare the agents of the invention. As used herein, the term "amine protecting group" means any group known in the art of organic synthesis for the protection of amine groups. Such amine protecting groups include those listed in Greene, "Protective Groups in Organic Synthesis" John Wiley & Sons, New York (1981) and "The Peptides: Analysis, Synthesis, Biology, Vol. 3, Academic Press, New York (1981). Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. Also included in the term "amine protecting group" are acyl groups such as azidobenzoyl, p-benzoylbenzoyl, o-benzylbenzoyl, p-acetylbenzoyl, dansyl, glycyl-p-benzoylbenzoyl, phenylbenzoyl, m-benzoylbenzoyl, benzoylbenzoyl.

In certain embodiments, the enzymatically cleavable oligopeptide can include oligo-L-arginine, oligo-L-lysine, oligo-L-aspartic acid or oligo-L-glutamic acid.

The enzymatically cleavable oligopeptide is cleavable by at least one enzyme selected from hydrolases, elastases, cathepsins, matrix metalloproteases, peptidases, exopeptidases, endopeptidases, carboxypeptidases, glycosidases, lipases, nucleases, lyases, amylases, phospholipases, phosphatases, phosphodiesterases, sulfatases, serine proteases, subtilisin, chymotrypsin, trypsin, threonine proteases, cysteine proteases, calpains, papains, caspases, aspartic acid proteases, pepsins, chymosins, glutamic acid proteases, renin, reductases, and parasitic, viral and bacterial enzymes.

IV. Biological Modifiers

Depending upon the intended use, the integrin agents can comprise one or more biological modifiers, which can alter the biological properties of the integrin agent. For example, the biological modifiers can render the integrin agents, for example, more water soluble, more dispersible in media for administration, increased binding specificity, less immunogenic, less toxic, reduced non-specific binding, altered biodistribution and pharmacokinetics compared to the unmodified integrin ligand.

For example, incorporation of methoxypolyethylene glycol (mPEG) or polypeptides may function to modify the pharmacodynamics and blood clearance rates of the integrin agents in vivo. Other biological modifiers can be chosen to accelerate the clearance of the integrin agents from background tissue, such as, muscle or liver, and/or from the blood, thereby reducing the background interference and improving image quality. Additionally, the biological modifiers can be used to favor a particular route of excretion, e.g., via the kidneys rather than via the liver. The biological modifiers can also aid in formulating probes in pharmaceutical compositions or may be used to alter or preserve the signal reporting properties of the integrin agents. In particular, chemical linking of polyethylene glycol (PEG) or a derivative thereof to integrin targeting agents can result in longer blood residence time (longer circulation) and decreased immunogenicity.

Exemplary biological modifiers include polyethylene glycol (PEG) and derivatives thereof (for example, alkoxy polyethylene glycol (for example, methoxypolyethylene glycol, ethoxypolyethylene glycol and the like), branched polypropylene glycol, polypropylene glycol, a graft copolymer of poly-lysine and methoxypolyethyleneglycol, amino acids, peptides, lipids, fatty acids, palmitate, phospholipids, phospholipid-PEG conjugates, carbohydrates (such as dextran, amino-dextran, carboxymethyl-dextran), iron oxide nanoparticles, sulfonates, polysulfonates, cysteic acid, naphthylalanine, phenylalanine, and 3,3-diphenylpropylamine.

In general, the biological modifier may have a molecular weight of from about 2 kDa to less than about 50 kDa, such as from about 5 kDa to about 40 kDa, such as from about 10 kDa to about 35 kDa, further such as from about 15 kDa to 30 kDa. In another embodiment, the biological modifier may have a molecular weight of from about 5 kDa to about 45 kDa, such as from about 5 kDa to about 40 kDa, such as from about 5 kDa to about 35 kDa, such as from about 5 kDa to about 30 kDa, such as from about 5 kDa to about 25 kDa, such as from about 5 kDa to about 20 kDa, such as from about 5 kDa to about 15 kDa, further such as from about 5 kDa to 10 kDa. In another embodiment, the biological modifier may have a molecular weight of from about 2 kDa to less than 50 kDa, such as from about 2 kDa to about 45 kDa, such as from about 2 kDa to about 40 kDa, such as from about 2 kDa to about 35 kDa, such as from about 2 kDa to about 30 kDa, such as from about 2 kDa to about 25 kDa, such as from about 2 kDa to about 10 kDa, further such as from about 2 kDa to 5 kDa.

In certain embodiments, as discussed above, the biological modifier may be a PEG moiety that has a molecular weight, for example, from about 0.5 kDa to about 50 kDa, from about 5 kDa to about 35 kDa, or from about 10 kDa to about 30 kDa. Alternatively, the PEG may be dPEG, functionalized at a discrete molecular weight, for example, of about 1100 daltons.

In certain embodiments, the PEG is methoxyPEG$_{(5000)}$-succinimidylpropionate (mPEG-SPA), methoxyPEG$_{(5000)}$-succinimidylsuccinate (mPEG-SS). Such PEGS are commercially available from Nektar Therapeutics or SunBiowest or LaysanBio or NOF.

The PEG moiety can be conjugated to reactive amines on the integrin agent via a carboxyl functionality. Alternatively, the PEG modifier can be conjugated to the integrin agent by using a thiol reactive cross linker and then reacting with a thiol group on the PEG.

In one embodiment, the PEG may be branched, or Y-shaped, as available from JenKem USA or NOF, or comb-shaped, or synthesized by coupling two or more PEGs to a small molecule such as glutamic acid.

The omega position of PEG may include a hydroxyl group or a methoxy group and the PEG may also contain an amino group in the omega position. Such an amino group can in turn be coupled to a variety of agents. In another embodiment of the present invention, the biological modifier can be a pegylated poly-L-lysine or a pegylated poly-D-lysine.

In other embodiments, the biological modifier can be polyvinylpyrrolidone (PVP)-type polymers. The biological modifier can be a functionalized polyvinylpyrrolidone, for example, carboxy or amine functionalized on one (or both) ends of the polymer (as available from Polymersource) or within the polymer chain.

Alternatively, the biological modifier can include Poly N-(2-hydroxypropyl)methacrylamide (HPMA), or functionalized HPMA (amine, carboxy, etc.), Poly(N-isopropyl acrylamide) or functionalized poly(N-isopropylacrylamide).

Biological modifiers can include straight or branched chain acyl groups, such as pentynoyl; acidic groups, such as succinyl; lower alkyl groups, such as methyl, ethyl, propyl, etc.; carboxyalkyl groups, such as carboxyethyl; haloalkyl groups, such as trifluoromethyl; and the like.

In general, the inclusion of the biological modifier should not adversely affect the affinity and/or binding properties of the integrin agents.

V. Exemplary Integrin Targeting Agents, and Formulations

Useful integrin targeting agents can be created using one or more of the integrin binding moieties, imaging reporters, biological modifiers, and linkers described hereinabove using standard chemistries known in the art. Depending upon the particular application, the integrin agents should be water soluble or water dispersible (i.e., sufficiently soluble or suspendable in aqueous or physiological media solutions). The in vivo half-life of the integrin agent can be designed to be at least about 10 minutes, but more preferably 30 minutes to several hours. The in vivo half-life of this agent preferably is a time (for example, at least about 30 minutes) sufficient to achieve good tissue exposure and binding. In one embodiment, the integrin agent is water soluble or dispersible in aqueous media, and is biocompatible, i.e., non-toxic having, for example, an $LD_{50}$ of greater than about 50 mg/kg body weight. The integrin agents preferably do not have any undesired phototoxic properties and/or display low serum protein binding affinity.

The imaging agents disclosed herein can be formulated into a pharmaceutical composition suitable for administration to a subject, for example, an animal and/or a human. The pharmaceutical composition can include one or more imaging agents and one or more excipients, for example, a stabilizer in a physiologically relevant carrier.

For in vivo use, the compositions of the present invention can be provided in a formulation suitable for administration to a subject, for example, an animal or a human. Accordingly, the formulations include the agents together with a physiologically relevant carrier suitable for the desired form and/or dose of administration. The term, "physiologically relevant carrier" is understood to mean a carrier in which the agents are dispersed, dissolved, suspended, admixed and physiologically tolerable, i.e., can be administered to, in, or on the subject's body without undue discomfort, or irritation, or toxicity. The preferred carrier is a fluid, preferably a liquid, more preferably an aqueous solution; however, carriers for solid formulations, topical formulations, inhaled formulations, ophthalmic formulations, and transdermal formulations are also contemplated as within the scope of the invention.

It is contemplated that the agents can be administered orally or parenterally. For parenteral administration, the agents can be administered intravenously, intramuscularly, cutaneously, percutaneously, subcutaneously, rectally, nasally, vaginally, and ocularly. Thus, the composition may be in the form of, e.g., solid tablets, capsules, pills, powders including lyophilized powders, colloidal suspensions, microspheres, liposomes granulates, suspensions, emulsions, solutions, gels, including hydrogels, pastes, ointments, creams, plasters, irrigation solutions, drenches, osmotic delivery devices, suppositories, enemas, injectables, implants, sprays, or aerosols. The pharmaceutical compositions can be formulated according to conventional pharmaceutical practice (see, e.g., Remington: The Science and Practice of Pharmacy, 20th edition, 2000, ed. A. R. Germaro, Lippincott Williams & Wilkins, Philadelphia, and Encyclopedia of Pharmaceutical Technology, eds. J. Swarbrick and J. C. Boylan, 1988-1999, Marcel Dekker, New York).

It is understood that the formulation of the agents, the choice of mode of administration, the dosages of agents administered to the subject, and the timing between administration of the agents and imaging is within the level of skill in the art.

VI. Applications

It is understood that integrin targeting agents can be used in a variety of imaging and therapeutic applications.

(a) Imaging Methods

The present invention provides methods for in vitro and in vivo imaging using the imaging agents disclosed herein. For a review of optical imaging techniques, see, e.g., Alfano et al., ANN. NY ACAD. SCI. 820:248-270 (1997); Weissleder, NATURE BIOTECHNOLOGY 19, 316-317 (2001); Ntziachristos et al., EUR. RADIOL. 13:195-208 (2003); Graves et al., CURR. MOL. MED. 4:419-430 (2004); Citrin et al., EXPERT REV. ANTICANCER THER. 4:857-864 (2004); Ntziachristos, ANN. REV. BIOMED. ENG. 8:1-33 (2006); Koo et al., CELL ONCOL. 28:127-139 (2006); and Rao et al., CURR. OPIN. BIOTECHNOL. 18:17-25 (2007).

Optical imaging includes all methods from direct visualization without use of any device and use of devices such as various scopes, catheters and optical imaging equipment, for example computer based hardware for tomographic presentations. The imaging agents are useful with optical imaging modalities and measurement techniques including, but not limited to: endoscopy; fluorescence endoscopy; luminescence imaging; time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

An imaging system useful in the practice of the invention typically includes three basic components: (1) an appropriate light source for inducing excitation of the imaging agent, (2) a system for separating or distinguishing emissions from light used for fluorophore excitation, and (3) a detection system. The detection system can be hand-held or incorporated into other useful imaging devices, such as intraoperative microscopes. Exemplary detection systems include an endoscope, catheter, tomographic system, hand-held imaging system, or a intraoperative microscope.

Preferably, the light source provides monochromatic (or substantially monochromatic) light. The light source can be a suitably filtered white light, i.e., bandpass light from a broadband source. For example, light from a 150-watt halogen lamp can be passed through a suitable bandpass filter commercially available from Omega Optical (Brattleboro, Vt.). Depending upon the system, the light source can be a laser. See, e.g., Boas et al., PROC. NATL. ACAD. SCI. USA 91:4887-4891, 1994; Ntziachristos et al., PROC. NATL. ACAD. SCI. USA 97:2767-2772, 2000; and Alexander, J. CLIN. LASER MED. SURG. 9:416-418, 1991. Information on lasers for imaging can be found, for example, at Imaging Diagnostic Systems, Inc., Plantation, Fla. and various other sources. A high pass or bandpass filter can be used to separate optical emissions from excitation light. A suitable high pass or bandpass filter is commercially available from Omega Optical, Burlington, Vt.

In general, the light detection system can be viewed as including a light gathering/image forming component and a light/signal detection/image recording component. Although the light detection system can be a single integrated device that incorporates both components, the light gathering/image forming component and light detection/image recording component are discussed separately.

A particularly useful light gathering/image forming component is an endoscope. Endoscopic devices and techniques which have been used for in vivo optical imaging of numerous tissues and organs, including peritoneum (Gahlen et al., J. PHOTOCHEM. PHOTOBIOL. B 52:131-135, 1999), ovarian cancer (Major et al., *Gynecol. Oncol.* 66:122-132, 1997), colon and rectum (Mycek et al., GASTROINTEST. ENDOSC. 48:390-394, 1998; and Stepp et al., ENDOSCOPY 30:379-386, 1998), bile ducts (Izuishi et al., HEPATOGASTROENTEROLOGY 46:804-807, 1999), stomach (Abe et al., ENDOSCOPY 32:281-286, 2000), bladder (Kriegmair et al., UROL. INT. 63:27-31, 1999; and Riedl et al., J. ENDOUROL. 13:755-759, 1999), lung (Hirsch et al., CLIN CANCER RES 7:5-220, 2001), brain (Ward, J. LASER APPL. 10:224-228, 1998), esophagus, and head and neck regions can be employed in the practice of the present invention.

Other types of light gathering components are catheter-based devices, including fiber optics devices. Such devices are particularly suitable for intravascular imaging. See, e.g., Tearney et al., SCIENCE 276:2037-2039, 1997; and CIRCULATION 94:3013, 1996.

Still other imaging technologies, including phased array technology (Boas et al., PROC. NATL. ACAD. SCI. USA 91:4887-4891, 1994; Chance, ANN. NY ACAD. SCI. 838:29-45, 1998), optical tomography (Cheng et al., OPTICS EXPRESS 3:118-123, 1998; and Siegel et al., OPTICS EXPRESS 4:287-298, 1999), intravital microscopy (Dellian et al., BR. J. CANCER 82:1513-1518, 2000; Monsky et al., CANCER RES. 59:4129-4135, 1999; and Fukumura et al., CELL 94:715-725, 1998), confocal imaging (Korlach et al., PROC. NATL. ACAD. SCI. USA 96:8461-8466, 1999; Rajadhyaksha et al., J. INVEST. DERMATOL. 104:946-952, 1995; and Gonzalez et al., J. MED. 30:337-356, 1999) and fluorescence molecular tomography (FMT) (Nziachristos et al., NATURE MEDICINE 8:757-760, 2002; U.S. Pat. No. 6,615,063, PCT WO 03/102558, and PCT WO 03/079015) can be used with the imaging agents of the invention. Similarly, the imaging agents can be used in a variety of imaging systems, for example, (1) the IVIS® Imaging Systems: 100 Series, 200 Series (Xenogen, Alameda, Calif.), (2) SPECTRUM and LUMINA (Xenogen, Alameda, Calif.), (3) the SoftScan® or the eXplore Optix™ (GE Healthcare, United Kingdom), (4) Maestro™ and Nuance™-2 Systems (CRi, Woburn, Mass.), (5) Image Station In-Vivo FX from Carestream Molecular Imaging, Rochester, N.Y. (formerly Kodak Molecular Imaging Systems), (6) OV100, IV100 (Olympus Corporation, Japan), (7) Cellvizio Mauna Kea Technologies, France), (8)] NanoSPECT/CT or HiSPECT (Bioscan, Washington, D.C.), (9) CTLM® or LILA™ (Imaging Diagnostic Systems, Plantation, Fla.), (10) DYNOT™ (NIRx Medical Technologies, Glen Head, N.Y.), and (11) NightOWL Imaging Systems by Berthold Technologies, Germany.

A variety of light detection/image recording components, e.g., charge coupled device (CCD) systems or photographic film, can be used in such systems. The choice of light detection/image recording depends on factors including the type of light gathering/image forming component being used. It is understood, however, that the selection of suitable components, assembling them into an optical imaging system, and operating the system is within ordinary skill in the art.

For agents that have magnetic properties, MRI imaging well known in the art can also be applied in the practice of the invention. For a review of MRI techniques, see, Westbrook, HANDBOOK OF MRI TECHNIQUE, $2^{nd}$ Edition, 1999, Blackwell Science. It is possible that images obtained, for example, by optical imaging and by magnetic resonance imaging can be co-registered or fused with one another to provide additional information about the item being imaged. Furthermore, multi-modality imaging systems (i.e., combined optical and MR imaging systems) can be used to create combined optical MR images.

In addition, the compositions and methods of the present invention can be used for other imaging compositions and methods. For example, the agents of the present invention can be imaged by other imaging modalities, such as, X-ray, computed tomography (CT), MR imaging, ultrasound, positron emission tomography (PET), and single photon computerized tomography (SPECT).

In addition, the compositions and methods of the present invention can be used in combination with other imaging compositions and methods. For example, the agents of the present invention can be imaged by optical imaging protocols either alone or in combination with other traditional imaging modalities, such as, X-ray, computed tomography (CT), MR imaging, ultrasound, positron emission tomography (PET), and single photon computerized tomography (SPECT). For instance, the compositions and methods of the present invention can be used in combination with CT or MRI to obtain both anatomical and molecular information simultaneously, for example, by co-registration of with an image generated by another imaging modality. The compositions and methods of the present invention can also be used in combination with X-ray, CT, PET, ultrasound, SPECT and other optical and MR contrast agents or alternatively, the agents of the present invention may also include imaging agents, such as iodine, gadolinium atoms and radioactive isotopes, which can be detected using CT, PET, SPECT, and MR imaging modalities in combination with optical imaging. The imaging agents can be linked to or incorporated in the agents.

(i) In Vivo Imaging Methods

With respect to optical in vivo imaging, such a method comprises (a) administering to a subject one or more of the integrin agents described herein, (b) allowing sufficient time to permit the agent to distribute with the subject, and (c) detecting a signal emitted by the integrin agent. The signal emitted by the agent can be used to construct an image, for example, a tomographic image. The foregoing steps can be repeated at predetermined time intervals thereby to permit evaluation of the emitted signals of the integrin agents in the subject over time.

In another in vivo imaging method, the method comprises the steps of (a) administering to a subject one or more of the integrin agents described herein that contains a fluorochrome; (b) allowing sufficient time to permit the integrin agent to distribute within the subject; (c) exposing the subject to light of a wavelength absorbable by the fluorochrome, and (d) detecting a signal emitted by the integrin agent. The foregoing steps can be repeated at predetermined time intervals thereby to permit evaluation of the emitted signals of the integrin agents in the subject over time. The illuminating and/or detecting steps (steps (c) and (d), respectively) can be performed using an endoscope, catheter, tomographic system, planar system, hand-held imaging system, goggles, or an intraoperative microscope.

Before or during these steps, a detection system can be positioned around or in the vicinity of a subject (for example, an animal or a human) to detect signals emitted from the subject. The emitted signals can be processed to construct an image, for example, a tomographic image. In addition, the processed signals can be displayed as images either alone or as fused (combined) images.

In addition, it is possible to practice an in vivo imaging method that selectively detects and images one, two or more molecular imaging probes, including the integrin agents simultaneously. In such an approach, for example, in step (a)

noted above, two or more imaging probes whose signal properties are distinguishable from one another are administered to the subject, either at the same time or sequentially, wherein at least one of the molecular imaging probes is a integrin agent. The use of multiple probes permits the recording of multiple biological processes, functions or targets.

The subject may be a vertebrate, for example, a mammal, for example, a human. The subject may also be a non-vertebrate (for example, C. elegans, drosophila, or another model research organism, etc.) used in laboratory research.

Information provided by such in vivo imaging approaches, for example, the presence, absence, or level of emitted signal can be used to detect and/or monitor a disease in the subject. Exemplary diseases include, without limitation, autoimmune disease, bone disease, cancer, cardiovascular disease, environmental disease, dermatological disease, immunologic disease, inherited disease, infectious disease, metabolic disease, neurodegenerative disease, ophthalmic disease, and respiratory disease. In addition, in vivo imaging can be used to assess the effect of a compound or therapy by using the imaging agents, wherein the subject is imaged prior to and after treatment with the compound or therapy, and the corresponding signal/images are compared.

The integrin targeting agents also can be used in in vivo imaging method where cells labeled with the integrin agent are administered to the recipient. The cells can be labeled with the integrin agents either in vivo or ex vivo. In the ex vivo approach, cells can be derived directly from a subject or from another source (e.g., from another subject, cell culture, etc.). The integrin agents can be mixed with the cells to effectively label the cells and the resulting labeled cells administered to the subject into a subject in step (a). Steps (b)-(d) then are followed as described above. This method can be used for monitoring trafficking and localization of certain cell types, including T-cells, tumor cells, immune cells and stem cells, and other cell types. In particular, this method may be used to monitor cell-based therapies.

It is understood that the formulation of the integrin targeting agents, the choice of mode of administration, the dosages of integrin agents administered to the subject, and the timing between administration of the integrin targeting agents and imaging is within the level of skill in the art.

The foregoing methods can be used to determine a number of indicia, including tracking the localization of the integrin agent in the subject over time or assessing changes or alterations in the metabolism and/or excretion of the integrin agent in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The methods and compositions of the invention can be used to help a physician or surgeon to identify and characterize areas of disease, such as arthritis, cancers and specifically colon polyps, or vulnerable or unstable plaque, to distinguish diseased and normal tissue, such as detecting tumor margins that are difficult to detect using an ordinary operating microscope, e.g., in brain surgery, to help dictate a therapeutic or surgical intervention, e.g., by determining whether a lesion is cancerous and should be removed or non-cancerous and left alone, or in surgically staging a disease, e.g., intraoperative lymph node staging, sentinel lymph node mapping, or assessing intraoperative bleeding.

The methods and compositions of the invention can also be used in the detection, characterization and/or determination of the localization of a disease, especially early disease, the severity of a disease or a disease-associated condition, the staging of a disease, and/or monitoring a disease. The presence, absence, or level of an emitted signal can be indicative of a disease state.

The methods and compositions of the invention can also be used to monitor and/or guide various therapeutic interventions, such as surgical procedures, and monitoring drug therapy, including cell based therapies. The methods of the invention can also be used in prognosis of a disease or disease condition.

With respect to each of the foregoing, examples of such disease or disease conditions that can be detected or monitored (before, during or after therapy) include inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, bone), cardiovascular disease (for example, atherosclerosis and inflammatory conditions of blood vessels, ischemia, stroke, thrombosis, disseminated intravascular coagulation), dermatologic disease (for example, Kaposi's Sarcoma, psoriasis, allergic dermatitis), ophthalmic disease (for example, macular degeneration, diabetic retinopathy), infectious disease (for example, bacterial, viral, fungal and parasitic infections, including Acquired Immunodeficiency Syndrome, malaria, Chagas Disease, Schistosomiasis), immunologic disease (for example, an autoimmune disorder, lymphoma, multiple sclerosis, rheumatoid arthritis, diabetes mellitus, lupus erythematosis, myasthenia gravis, Graves disease), central nervous system disease (for example, a neurodegenerative disease, such as Parkinson's disease or Alzheimer's disease, Huntington's Disease, amyotrophic lateral sclerosis, prion disease), inherited diseases, metabolic diseases, environmental diseases (for example, lead, mercury and radioactive poisoning, skin cancer), bone-related disease (for example, osteoporosis, primary and metastatic bone tumors, osteoarthritis), neurodegenerative disease, and surgery-related complications (such as graft rejection, organ rejection, alterations in wound healing, fibrosis or other complications related to surgical implants).

The methods and compositions described herein can, therefore, be used, for example, to determine the presence and/or localization of tumor cells, the presence and/or localization of inflammation, including the presence of activated macrophages, for instance in atherosclerosis or arthritis, the presence and in localization of vascular disease including areas at risk for acute occlusion (i.e., vulnerable plaques) in coronary and peripheral arteries, regions of expanding aneurysms, unstable plaque in carotid arteries, and ischemic areas. The methods and compositions of the invention can also be used in identification and evaluation of cell death, injury, apoptosis, necrosis, hypoxia and angiogenesis. The methods and compositions can also be used for drug delivery and to monitor drug delivery, especially when drugs or drug-like molecules are chemically attached to the fluorescent probes. Exemplary drug molecules include chemotherapeutic and cytostatic agents and photodynamic agents including but not limited to Photofrin, Lutrin, Antrin, aminolevulinic acid, hypericin, benzoporphyrin derivative, and porphyrins.

In addition, the methods and compositions described herein can be used to image angiogenesis (new blood vessel formation) in a subject. The method comprises administering to a subject (for example, a human or animal) an amount of one or more of the integrin agents described herein sufficient to facilitate angiogenesis imaging. After sufficient time to permit the agent to distribute within the animal or distribute within the area to be imaged, the presence and/or amount of the agent is determined. The presence and/or amount of the agent can then be used to create an image, for example, a tomographic image, representative of new blood vessel formation in the subject.

(ii) In Vitro Imaging Methods

With respect to in vitro imaging, the imaging agents can be used in a variety of in vitro assays. For example, an exemplary in vitro imaging method comprises: (a) contacting a sample, for example, a biological sample, with one or more of the integrin agents described herein; (b) allowing the agent(s) to interact with a biological target in the sample; (c) optionally, removing unbound agent; and (d) detecting a signal emitted from the agent thereby to determine whether the agent has been activated by or bound to the biological target. When the integrin agent comprises a fluorochrome, step (d) further comprises illuminating the sample with light of a wavelength absorbable by the fluorochrome to produce the emitted signal.

After an agent has been designed, synthesized, and optionally formulated, it can be tested in vitro by one skilled in the art to assess its biological and performance characteristics. For instance, different types of cells grown in culture can be used to assess the biological and performance characteristics of the agent. Cellular uptake, binding or cellular localization of the agent can be assessed using techniques known in the art, including, for example, fluorescent microscopy, FACS analysis, immunohistochemistry, immunoprecipitation, in situ hybridization and Forster resonance energy transfer (FRET) or fluorescence resonance energy transfer. By way of example, the agents can be contacted with a sample for a period of time and then washed to remove any free agents. The sample can then be viewed using an appropriate detection device such as a fluorescent microscope equipped with appropriate filters matched to the optical properties of a fluorescent agent. Fluorescence microscopy of cells in culture or scintillation counting is also a convenient means for determining whether uptake and binding has occurred. Tissues, tissue sections and other types of samples such as cytospin samples can also be used in a similar manner to assess the biological and performance characteristics of the agents. Other detection methods include, but are not limited to flow cytometry, immunoassays, hybridization assays, and microarray analysis, can also be used in the practice of the invention.

(b) Therapeutic Applications

Certain of the integrin targeting agents described herein, for example, agents containing a radiolabel and/or a drug molecule, can be used to ameliorate a symptom of, or treat, a particular disease or disorder. The method comprises (a) administering to a subject an amount of one or more the agents described herein sufficient to impart a therapeutic effect in the subject; and (b) permitting sufficient time for the agent to distribute within the subject or otherwise localize in a region of the subject to be treated and then, (c) depending upon the therapeutic agent, optionally activating the agent to impart a therapeutic effect. For example, when the therapeutic agent is a radiolabel, no subsequent activation is required. However, when the therapeutic agent is a photoreactive agent, for example, a dye used in photodynamic therapy, the agent may be activated by exposing the agent to light having a wavelength that activates the agent. As a result, the agents can be used to treat a condition of interest, for example, a cancer, immune disorder, inflammatory disorder, vascular disorder and the like. Furthermore, the agents can be used to prevent, ameliorate, or reverse angiogenesis in a region of interest in the subject.

The invention will now be illustrated by means of the following examples, which are given for the purpose of illustration only and without any intention to limit the scope of the present invention.

EXAMPLES

The following non limiting examples demonstrate the synthesis of exemplary integrin targeting agents. Representative materials and methods that may be used in preparing the materials of the invention are described further below. All chemicals and solvents (reagent grade) were used as commercially obtained without further purification. HPLC Analysis: Analytical RP HPLC was performed on a Waters 2695 system using either a Phenomenex Phenyl-hexyl column (3µ, 100× 4.6 mm) or C18 column (5µ, 250×4.6 mm) with a flow rate of 1 mL/min. A linear gradient of A (10 mM triethylamine acetate, pH=7, +5% acetonitrile) and B (acetonitrile) was used. Typically, the gradient started at 10-40% of B and changed to 50-90% of B over 10 to 20 min. Chromatograms were monitored at 254 nm and 675 nm. Preparative HPLC was performed on a Varian system using a Phenomenex C18 column (250×10 mm) at 4.7 mL/min using similar gradient as the analytical run.

Example 1

Synthesis of Imaging Targeting Moiety Compound 6

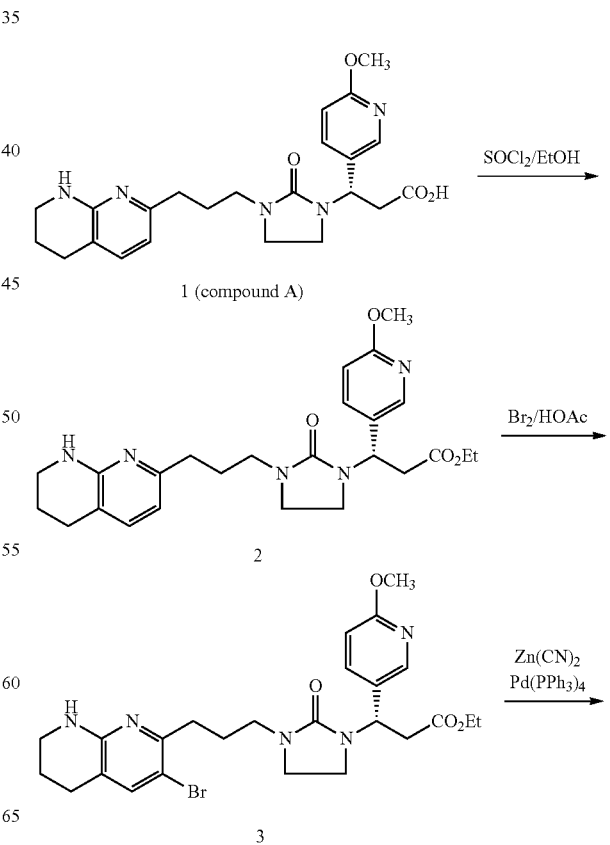

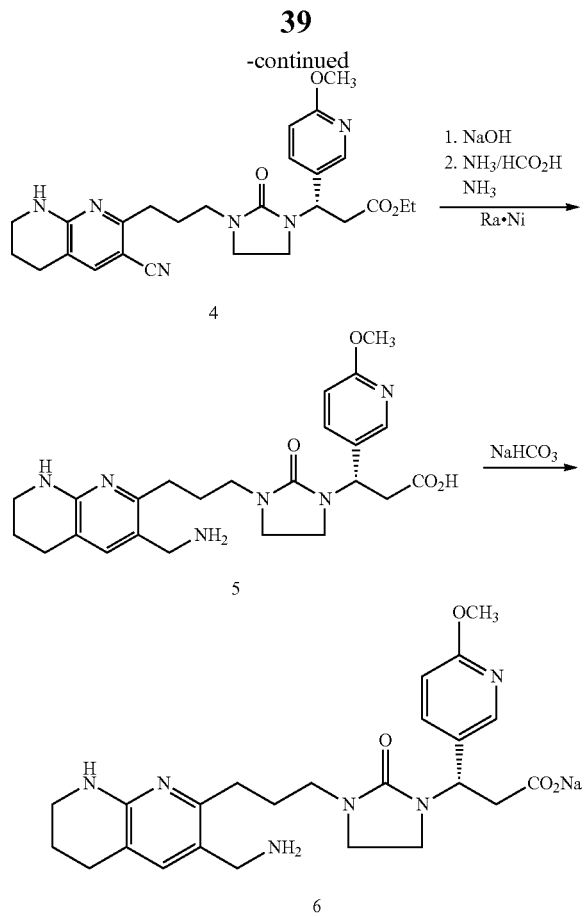

Part A: Preparation of Compound 2

Thionyl chloride (1.3 g, 10.9 mmol) was added to 20 mL of an ethanolic solution containing compound 1 (690 mg, 1.57 mmol). The solution was stirred at 40-45° C. after addition, and the reaction was monitored by HPLC. After reaction completion (approximately 45 minutes), the solution was concentrated to an oil, and ethyl acetate (30 mL) and water (20 mL) were added. The mixture was neutralized with solid sodium bicarbonate until pH ~8. After phase separation, the aqueous layer was extracted with 2×15 mL of ethyl acetate. The combined ethyl acetate solution was washed with 2×10 mL of saturated brine and dried over anhydrous sodium sulfate. The solid was filtered off and the filtrate was concentrated to provide 820 mg (111% mass balance) of ester 2 as an oil.

Part B: Preparation of Compound 3

Ester 2 (820 mg, 1.57 mmol theory) was dissolved in 4 mL of acetic acid, and then bromine (296 mg, 1.85 mmol) was added. HPLC analysis showed the reaction was complete after about 10 minutes. The solution was diluted with ethyl acetate (30 mL) and water (20 mL). The mixture was neutralized with sodium bicarbonate until pH ~7. After phase separation, the aqueous layer was extracted with 20 mL of ethyl acetate. The combined ethyl acetate was washed with 2×20 mL of saturated brine, and dried over sodium sulfate. Evaporation of solvent afforded compound 9 as an off-white solid (908 mg, 118% mass balance).

Part C: Preparation of Compound 4

Compound 9 (908 mg, 1.57 mmol theory) was mixed with zinc cyanide (380 mg, 3.2 mmol), and tetrakis(triphenylphosphine)palladium (0) (365 mg, 0.31 mmol) in dimethyl acetamide (4 mL) and the resulting mixture was purged four times with vacuum/nitrogen. The mixture was heated at ~120° C. for 20 hours and HPLC showed >97% conversion. After cooling to ~20° C., 30 mL ethyl acetate was added. The solid was filtered and washed with 2×25 mL of ethyl acetate. The combined ethyl acetate solution was washed with 2×20 mL of water and 20 mL of saturated brine. After drying over sodium sulfate, the solution was concentrated to an oil. The residue was dissolved in 10 mL of ethyl acetate and isolated through a silica gel column (70 mL bed volume), eluted with 8% methanol in ethyl acetate (v/v). The appropriate fractions were combined and concentrated to dryness to provide cyano-ester 4 as a waxy solid (510 mg, 66% overall)

Part D: Preparation of Compound 5

Cyano ester 4 (170 mg, 0.345 mmol) was dissolved in methanol (3 mL), and 1 M aqueous sodium hydroxide (2 mL) was added. The solution was aged at 20° C. until HPLC showed complete hydrolysis of 4 (formation of methyl ester was also observed, which also hydrolyzed to the cyano acid intermediate). The solution was concentrated to dryness and the residue dissolved in an ammonia/methanol solution (3.5 M, 10 mL). The resulting solution was added to Raney Ni (~100 mg, washed 3×'s with methanol prior to addition) in a pressure tube. Ammonium formate (120 mg, 1.9 mmol) was added to the mixture, which was then stirred vigorously (stir bar) at 20° C. until HPLC showed complete conversion of the cyano acid intermediate (~20 hours). The supernatant was removed and the catalyst was washed with 4×10 mL of methanol. The combined methanol solution was concentrated to dryness. The solid was dissolved in 10 mL of 30/70 methanol/water (v/v) and loaded to an ion exchange column (Dowex® 50WX8-200, 5 mL bed volume) to remove nickel ion. The resin was washed with water until pH ~6 and eluted with 1 M ammonia in 30/70 methanol/water. The appropriate fractions were combined and evaporated to afford the amino acid 5 (110 mg), which might exist as a partial ammonium salt. MALDI-MS calculated 468.6 for $C_{24}H_{32}N_6O_4$. Found 469.7.

Part E: Preparation of Imaging Targeting Moiety Compound 6

The crude amino acid 5 (90 mg, 0.185 mmol as the ammonium salt) was dissolved in 10 mL of 1:1 methanol/water, and then sodium bicarbonate (16 mg, 0.185 mmol) was added. The resulting solution was evaporated to dryness to afford sodium salt 6 (97 mg, 0.20 mmol) as an off-white solid.

Example 2

Synthesis of Compound 12

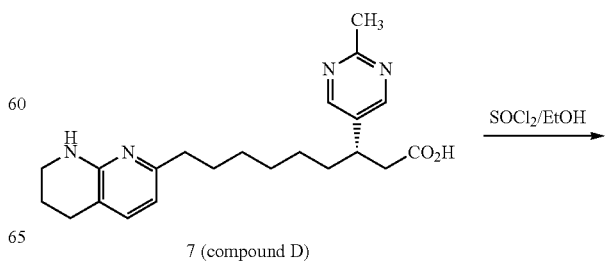

7 (compound D)

-continued

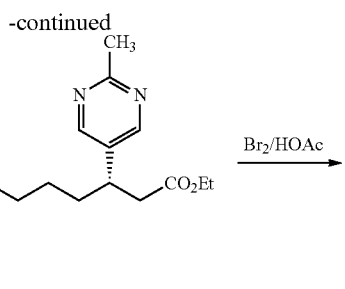

8

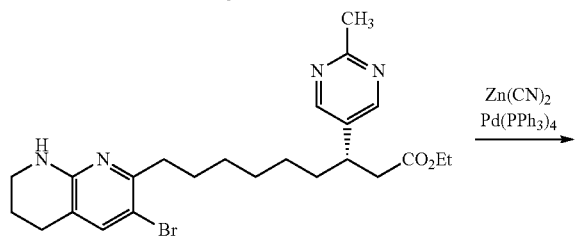

9

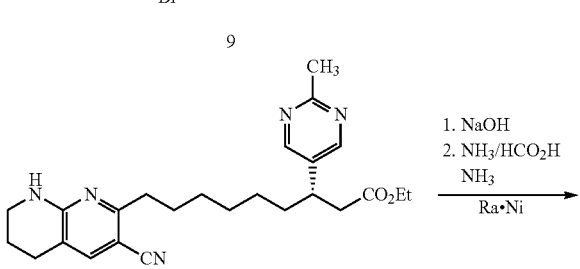

10

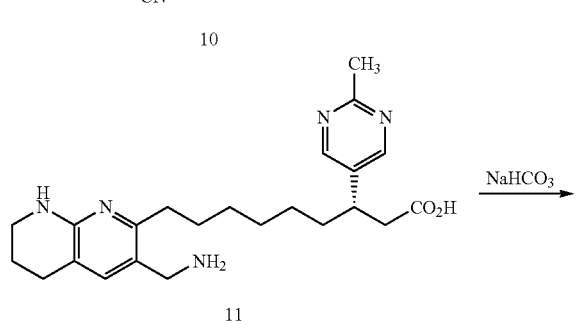

11

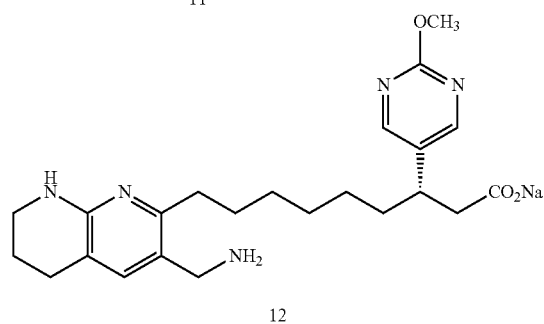

12

Part A: Preparation of Compound 8

Thionyl chloride (1.2 g, 10 mmol) was added slowly to 20 mL of an ethanolic solution of compound 7 (764 mg, 2.0 mmol). The solution was stirred at 40-45° C. after addition and the reaction was monitored by HPLC. After completion of the reaction (approximately 3 hours), the solution was concentrated to an oil and ethyl acetate 20 mL) and water (10 mL) were added. The mixture was neutralized with solid sodium bicarbonate until pH ~8. After phase separation the aqueous layer was extracted with 20 mL of ethyl acetate. The combined ethyl acetate solution was washed with 2×10 mL of saturated brine and dried over anhydrous sodium sulfate. The solid was filtered off and the filtrate was concentrated to provide 762 mg (1.86 mmol, 93%) of compound 8 as an oil.

Part B: Preparation of Compound 9

Ester 8 (762 mg, 1.86 mmol) was dissolved in 3.5 mL of acetic acid and then bromine (340 mg, 2.1 mmol) was added. HPLC analysis showed the reaction was completed after 20 minutes. The solution was diluted with ethyl acetate (30 mL) and water (25 mL). The mixture was neutralized with sodium bicarbonate until pH ~7. After phase separation, the aqueous layer was extracted with 20 mL of ethyl acetate. The combined ethyl acetate was washed with 2×15 mL of saturated brine and dried over sodium sulfate. Evaporation of solvent afforded compound 9 as an oil (854 mg, 94%), which solidified upon standing. MALDI-MS calculated 489.5 for $C_{24}H_{33}BrN_4O_2$. Found 491.8.

Part C: Preparation of Compound 10

Compound 9 (854 mg, 1.7 mmol) was mixed with zinc cyanide (590 mg, 5.0 mmol), and tetrakis(triphenylphosphine)palladium (0) (570 mg, 0.49 mmol) in dimethyl acetamide (5 mL) and the resulting mixture was purged four times with vacuum/nitrogen. The mixture was heated at ~110° C. for 18 hours and HPLC showed >99% conversion. After cooling to ~20° C., ethyl acetate (30 mL) was added. The solid was harvested by filtration and washed with 2×25 mL of ethyl acetate. The combined ethyl acetate solution was washed with 2×20 mL of water and 20 mL of brine. After drying over sodium sulfate, the solution was concentrated to an oil. The residue was dissolved in 10 mL of ethyl acetate and isolated through a silica gel column (70 mL bed volume), eluted with 3% methanol in ethyl acetate (v/v). The appropriate fractions were combined and concentrated to dryness to provide cyano ester 10 as a solid (710 mg, 93%). MALDI-MS calculated 435.6 for $C_{25}H_{33}N_5O_2$. Found 438.9.

Part D: Preparation of Compound 11

Cyano ester 10 (200 mg, 0.46 mmol) was dissolved in methanol (7 mL) and 1 M aqueous sodium hydroxide (3 mL) was added. The solution was aged at 20° C. until HPLC showed complete hydrolysis of the ester (formation of methyl ester was also observed, which also hydrolyzed to the cyano acid intermediate). The solution was concentrated to dryness and the residue dissolved in an ammonia/methanol solution (3.5 M, 15 mL). The resulting solution was added to Raney Ni (~150 mg, washed 3×'s with methanol prior to addition) in a pressure tube. To the mixture was added ammonium formate (200 mg, 3.2 mmol). The mixture was stirred vigorously (stir bar) at 20° C. until HPLC showed complete conversion of the cyano acid intermediate (~20 h). The supernatant was removed and the catalyst was washed with 4×10 mL of methanol. The combined methanol solution was concentrated to dryness. The solid was dissolved in 10 mL of 30/70 methanol/water (v/v) and loaded to an ion exchange column (Dowex® 50WX8-200, 5 mL bed volume) to remove nickel ion. The resin was washed with water until pH ~6 and eluted with 1 M ammonia in 30/70 methanol/water. The appropriate fractions were combined and evaporated to afford the amino acid 11 (143 mg), which might exist as a partial ammonium salt. LC/MS calculated 411.5 for $C_{23}H_{33}N_5O_2$. Found 410 (negative mode).

Part E: Preparation of Compound 12

The crude amino acid 11 (130 mg, 0.30 mmol as the ammonium salt) was dissolved in 20 mL of 1:1 methanol/water, and then sodium bicarbonate (25 mg, 0.3 mmol) was added. The resulting solution was evaporated to dryness to afford sodium salt 12 (103 mg, 0.23 mmol) as an off-white solid.

Example 3

Preparation of Imaging Agent E-3

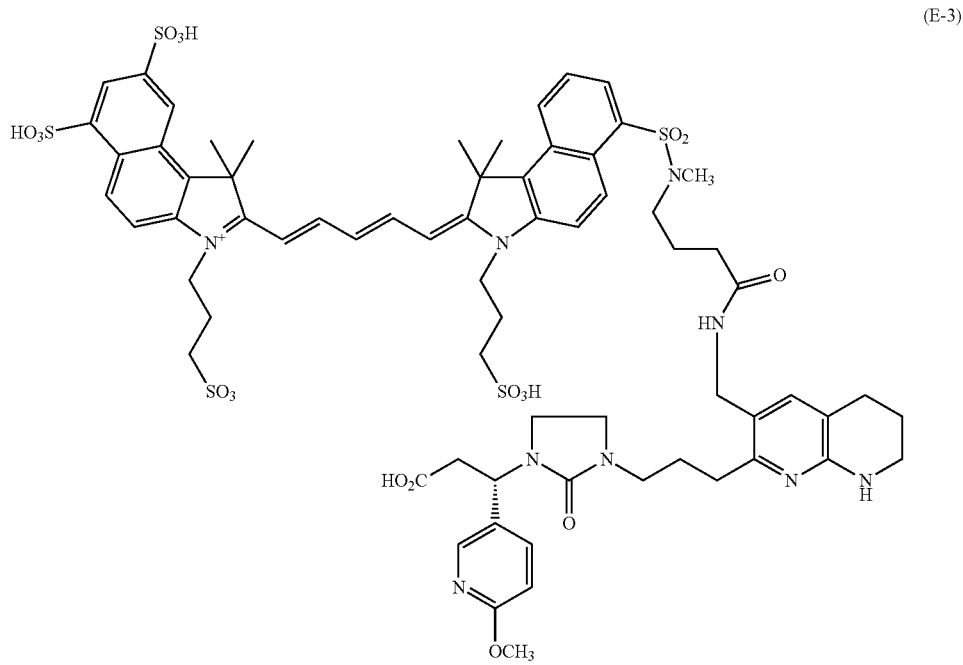

(E-3)

The fluorophore C1 (see Table 2, 1-1.5 µmol) was added to a solution containing compound 6 (~3 mg) and N-ethyl morpholine (10 µL) in DMSO (0.7 mL). The solution was aged at 20° C. for 1-2 hours. The product was precipitated by addition of 1:1 ethyl acetate/hexane (~10 mL) and washed with MTBE (2×5 mL). The solid was dissolved in water and purified by preparative HPLC and isolated as a blue solid after evaporation of the preparative HPLC fraction. MALDI-MS calculated 1487 for $C_{68}H_{81}N_9O_{19}S_5$. Found 1489.

Example 4

Preparation of Imaging Agent E-4

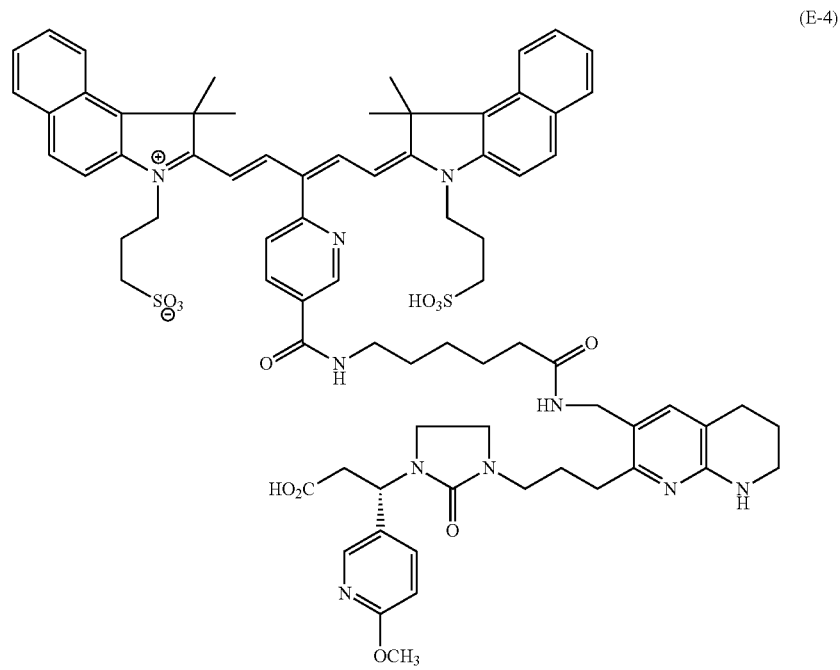

(E-4)

An active ester of fluorophore A1 (see Table 2, 1-1.5 μmol) was added to a solution of compound 6 (~3 mg) and N-ethyl morpholine (10 μL) in DMSO (0.7 mL). The solution was aged at 20° C. for 1-2 hours. The product was precipitated by addition of 1:1 ethyl acetate/hexane (~10 mL) and washed with MTBE (2×5 mL). The solid was dissolved in water and purified by preparative HPLC and isolated as a blue solid after evaporation of the preparative HPLC fraction. MALDI-MS calculated 1382 for $C_{75}H_{86}N_{10}O_{12}S_2$. Found 1385.

Example 5

Preparation of Imaging Agent E-5

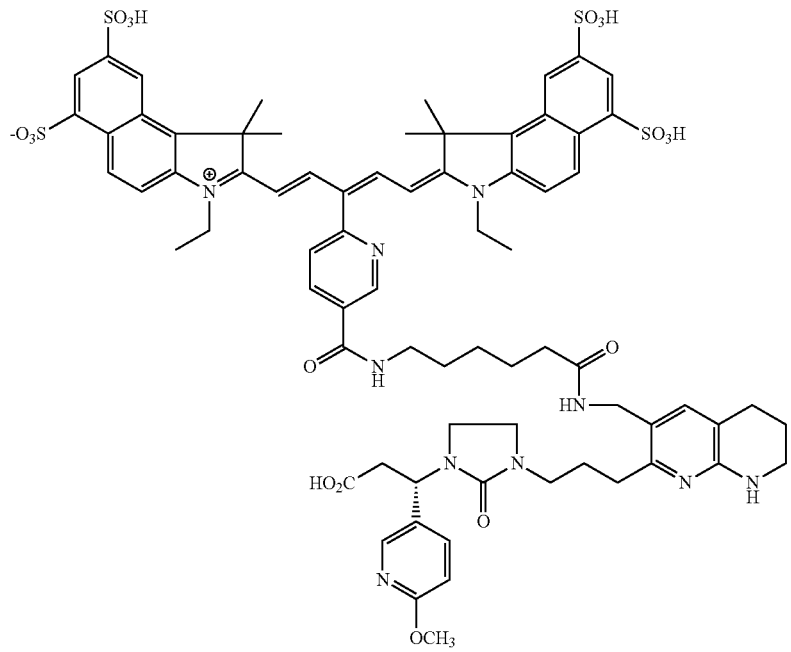

(E-5)

An active ester of the fluorochrome E1 (see Table 2, 1-1.5 μmol) was added to a solution of compound 6 (~3 mg) and N-ethyl morpholine (10 μL) in DMSO (0.7 mL). The solution was aged at 20° C. for 1-2 hours. The product was precipitated by addition of 1:1 ethyl acetate/hexane (~10 mL) and washed with MTBE (2×5 mL). The solid was dissolved in water and purified by preparative HPLC and isolated as a blue solid after evaporation of the preparative HPLC fraction. MALDI-MS calculated 1514 for $C_{73}H_{82}N_{10}O_{18}S_4$. Found 1518.

Example 6

Preparation of Imaging Agent E-6

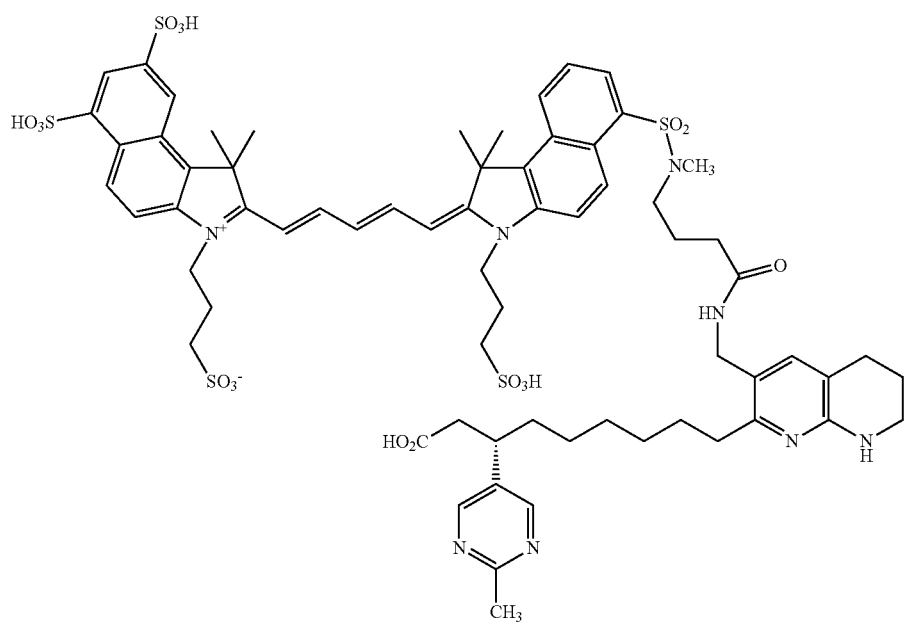

(E-6)

Fluorophore C1 (see Table 2, 1-1.5 μmol) was added to a solution of compound 12 (~3 mg) and N-ethyl morpholine (10 μL) in DMSO (0.7 mL). The solution was aged at 20° C. for 1-2 hours. The product was precipitated by addition of 1:1 ethyl acetate/hexane (~10 mL) and washed with MTBE (2×5 mL). The solid was dissolved in water and purified by preparative HPLC and isolated as a blue solid after evaporation of the preparative HPLC fraction. MALDI-MS calculated 1430 for $C_{67}H_{82}N_8O_{17}S_5$. Found 1434.

Example 7

Preparation of Imaging Agent E-7

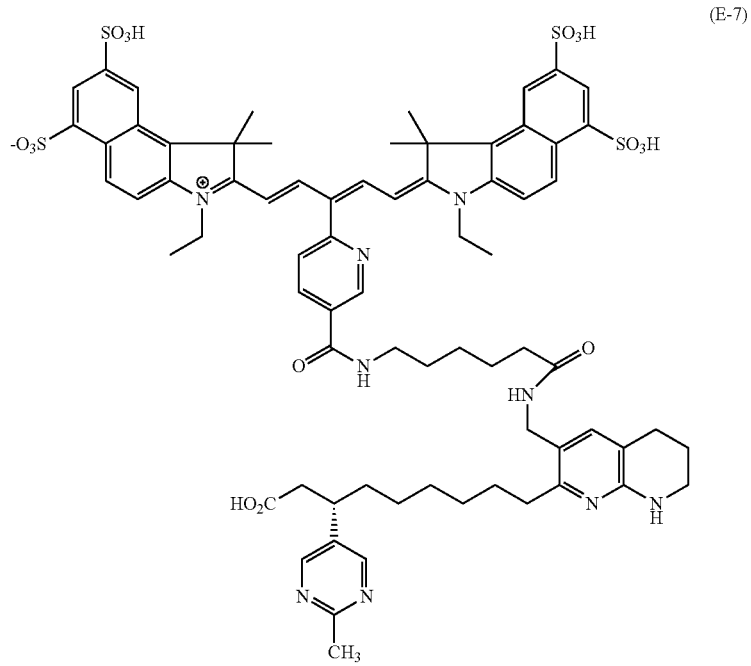

(E-7)

An active ester of the fluorophore E1 (see Table 2, 1-1.5 μmol) was added to a solution of 12 (~3 mg) and N-ethyl morpholine (10 μL) in DMSO (0.7 mL). The solution was aged at 20° C. for 1-2 hours. The product was precipitated by addition of 1:1 ethyl acetate/hexane (~10 mL) and washed with MTBE (2×5 mL). The solid was dissolved in water and purified by preparative HPLC and E-7 isolated as a blue solid after evaporation of the preparative HPLC fraction. MALDI-MS calculated 1457 for $C_{72}H_{83}N_9O_{16}S_4$. Found 1460.

Example 8

Preparation of Imaging Agent E-8

AlexaFluor750 NHS ester (1-1.5 μmol) was added to a solution of compound 12 (~3 mg) and N-ethyl morpholine (10 μL) in DMSO (0.7 mL). The solution was aged at 20° C. for 1-2 hours. The product was precipitated by addition of 1:1 ethyl acetate/hexane (~10 mL) and washed with MTBE (2×5 mL). The solid was dissolved in water and purified by preparative HPLC and compound E-8 isolated as a greenish-blue solid after evaporation of the preparative HPLC fraction. MALDI-MS calculated 1278. Found 1279.

Example 9

Preparation of Imaging Agent E-9

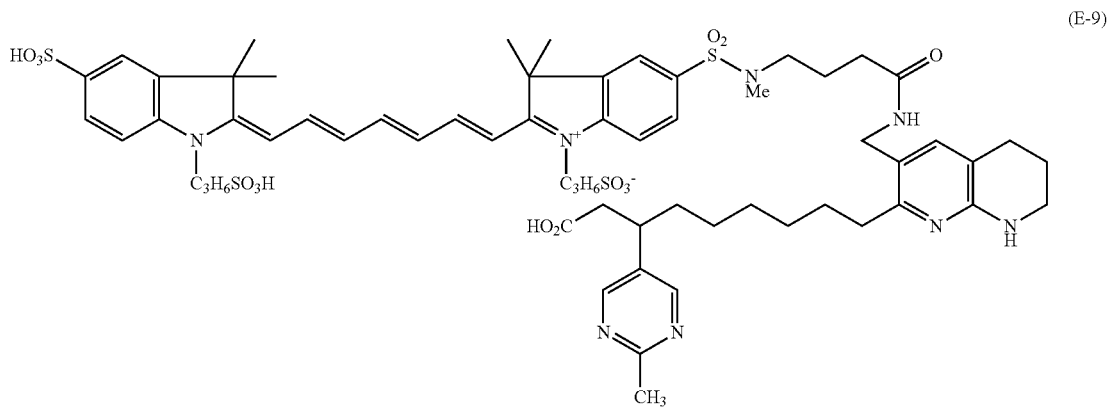

(E-9)

Fluorophore B1 (see Table 2, 1-1.5 μmol) was added to a solution of compound 12 (~3 mg) and N-ethyl morpholine (10 μL) in DMSO (0.7 mL). The solution was aged at 20° C. for 1-2 hours. The product was precipitated by addition of 1:1 ethyl acetate/hexane (~10 mL) and washed with MTBE (2×5 mL). The solid was dissolved in water and purified by preparative HPLC and compound E-9 isolated as a greenish-blue solid after evaporation of the preparative HPLC fraction.

LC/MS calculated 1276.5 for $C_{61}H_{80}N_8O_{14}S_4$. Found 1276 (-ve mode)

Example 10

Preparation of Imaging Agent E-10

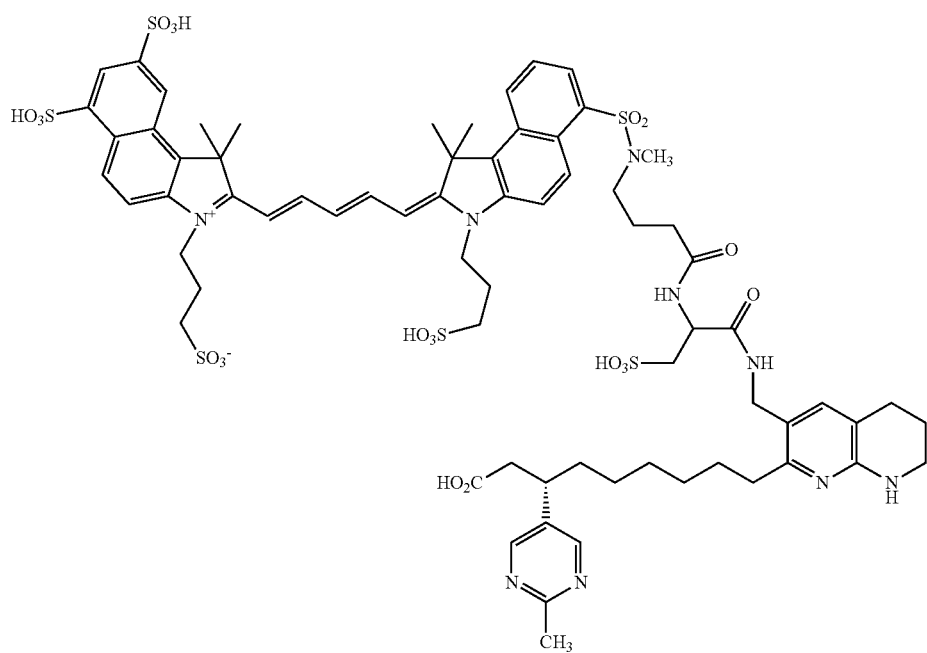

(E-10)

Reaction of fluorophore C1 (see Table 2) with L-cysteic acid (Csa) in the presence of triethylamine produced the compound of formula C1-Csa after preparative HPLC purification, which was converted to the N-hydroxysuccinimide ester with DSC/DMAP in DMSO. The NHS ester was precipitated with MTBE. Reaction of the resulting NHS ester with compound 12 produced compound E-10, which was purified by preparative HPLC and isolated. LC/MS calculated 1581.5 for $C_{70}H_{87}N_9O_2S_6$. Found 1580.9 (-ve mode).

Example 11

Preparation of Imaging Agent E-11

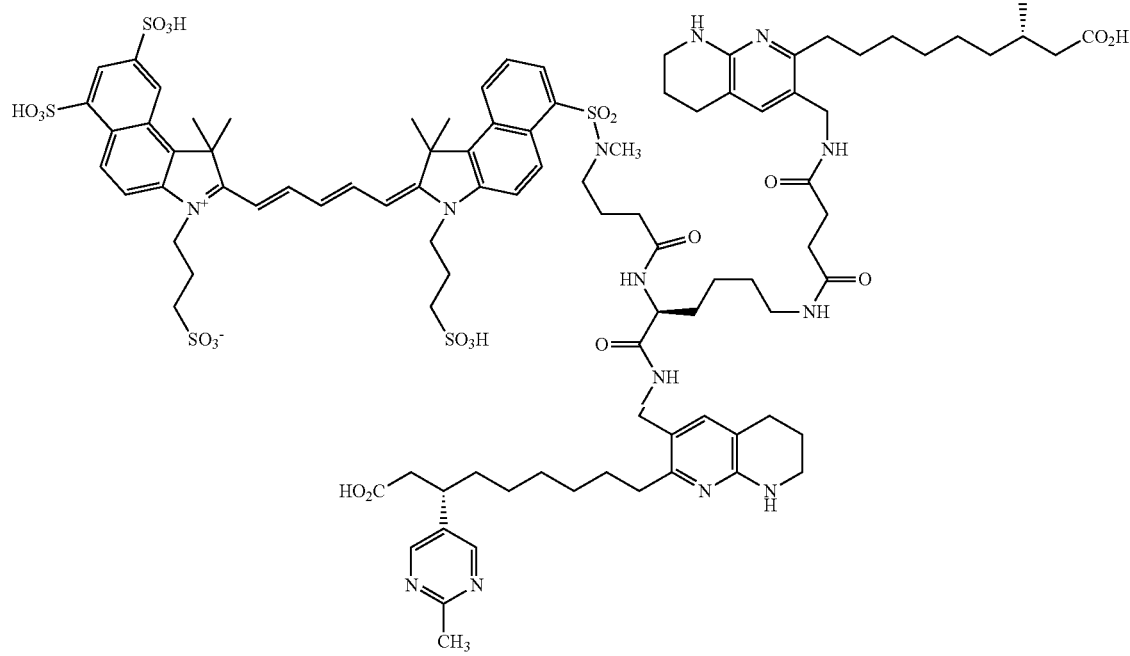

(E-11)

Part A. Preparation of Integrin Imaging Moiety Compound 13.

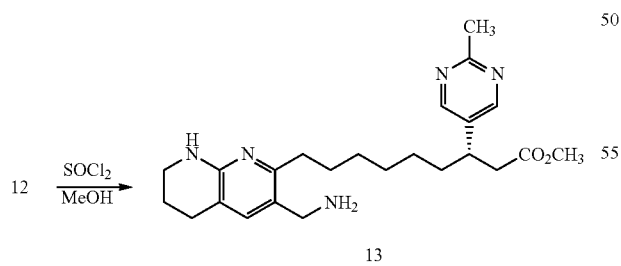

Thionyl chloride (50 μL, 81.5 mg, 0.68 mmol) was added slowly to the sodium salt of compound 12 (55 mg, 0.12 mmol) suspended in 2 mL of methanol. The solid dissolved initially and a precipitate was formed. After aging at ~20° C. for 30 minutes, HPLC showed complete conversion of the starting material. The mixture was concentrated to provide ester 13 as the HCl salt (60 mg).

Part B. Preparation of Compound 15.

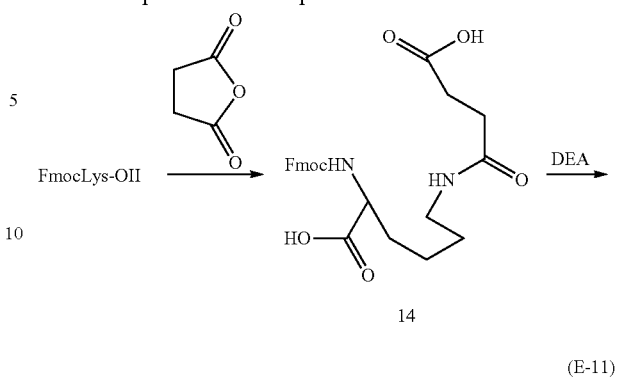

N-ethyl morpholine (0.35 mL, 318 mg, 2.77 mmol) was added to a slurry of Fmoc-Lys-OH (368 mg, 1.0 mmol) in 9 mL of 1:2 water/acetonitrile. Succinic anhydride (125 mg, 1.25 mmol) was then added. The solid dissolved slowly and HPLC showed complete reaction after 18 hours at ~20° C. The solution was concentrated to an oil and diluted with 2 mL of water. The product precipitated upon addition of aqueous HCl (2 N, 3 mL). The solid was collected by filtration and washed with 3×5 mL of water. The solid was air-dried to constant weight to provide FmocLys(Suc), 14, as an off-white solid (462 mg). MALDI-MS calculated 491.2 for $C_{25}H_{28}N_2NaO_7$. Found 490.4.

Diethylamine (1.5 mL, 1.1 g, 15 mmol) was added to a solution of compound 14 (100 mg, 0.21 mmol) in 5 mL of acetonitrile. A fine slurry was formed and HPLC indicated complete reaction after 4 hours. The mixture was concentrated to a solid and washed with 3×3 mL of MTBE. The solid was flushed 2× with triethylamine (0.15 mL) in methanol (5 mL) and triethylamine (0.2 mL) in 8 mL of 1:1 acetonitrile/methanol. Compound 15 was obtained as a off-white solid after drying to constant weight (48 mg).

Part C. Preparation of Imaging Agent Compound E-11

Reaction of the fluorophore C1 (see Table 2) with compound 15 in the presence of triethylamine produced the di-carboxylic acid, C1-15, as a blue solid after preparative HPLC purification.

MALDI-MS calculated 1265 for $C_{54}H_{67}N_5O_{20}S_5$. Found 1267. Coupling of C1-15 with methyl ester 13 mediated by HBTU/triethylamine produced the (di)methyl ester conjugate as a blue solid after preparative HPLC purification. MALDI-MS calculated 2080 for $C_{102}H_{133}N_{15}O_{22}S_5$. Found 2082. The methyl ester was hydrolyzed with NaOH (0.1 N in 1:1 MeOH/water, 3 hr at 20° C.) and the probe was purified by preparative HPLC to give E-11. MALDI-MS calculated 2052 for $C_{100}H_{129}N_{15}O_{22}S_5$. Found 2055.

Example 12

Preparation of DOTA Conjugate of Compound 12 (E-12) and $^{111}$In Labeling

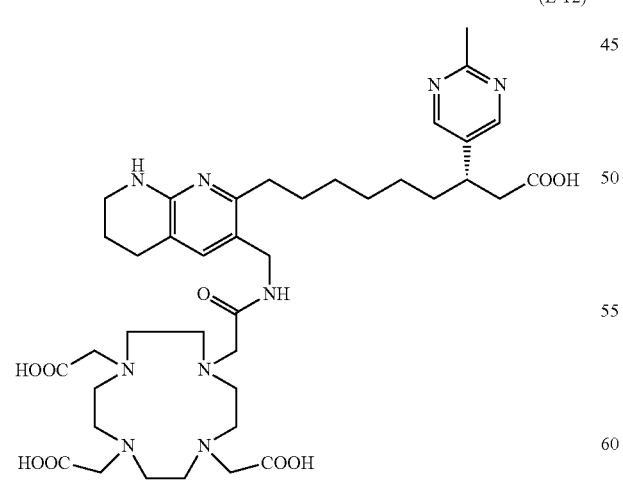

(E-12)

DOTA Succinimidyl ester (Macrocyclics, TX) (1-1.5 µmol) was added to a solution of compound 12 (~3 mg) and N-ethyl morpholine (10 µL) in DMSO (0.7 mL). The solution is aged at 20° C. for 1-2 hours. The product is precipitated by addition of 1:1 ethyl acetate/hexane (~10 mL) and washed with MTBE (2×5 mL). The solid is dissolved in water and purified by preparative HPLC and compound E-12 is isolated as a solid after evaporation of the preparative HPLC fraction. Approximately 50 µL of $^{111}$InCl$_3$ (about 100 mCi/mL in 0.05 M HCl) is combined with an equal volume of freshly prepared 1.0 M ammonium acetate, after which 0.1-1 mg of E-12 dissolved in 0.25 mL water is added. The reaction is allowed to proceed at room temperature for 30 minutes. The product is analyzed by HPLC.

Example 13

Preparation of DOTA Conjugate of Compound 6 (E-13) and $^{111}$In Labeling

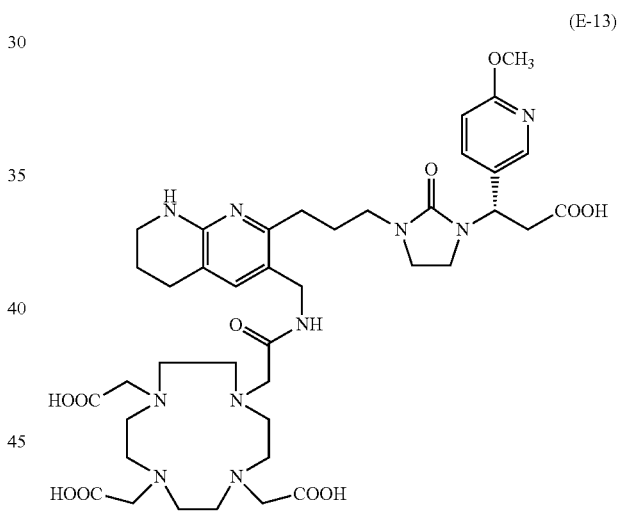

(E-13)

DOTA Succinimidyl ester (Macrocyclics, TX) (1-1.5 µmol) is added to a solution containing compound 6 (~3 mg) and N-ethyl morpholine (10 µL) in DMSO (0.7 mL). The solution is aged at 20° C. for 1-2 hours. The product is precipitated by addition of 1:1 ethyl acetate/hexane (~10 mL) and washed with MTBE (2×5 mL). The solid is dissolved in water and purified by preparative HPLC and compound E-13 is isolated as a solid after evaporation of the preparative HPLC fraction. About 50 µL of $^{111}$InCl$_3$ (about 100 mCi/mL in 0.05 M HCl) is combined with an equal volume of freshly prepared 1.0 M ammonium acetate, after which 0.1-1 mg of the reagent E-13 dissolved in 0.25 mL water is added. The reaction is allowed to proceed at room temperature for 30 minutes. The product is analyzed by HPLC.

Example 14

Preparation of Hynic Conjugate of Compound 12 (E-14) and $^{99m}$Tc Labeling

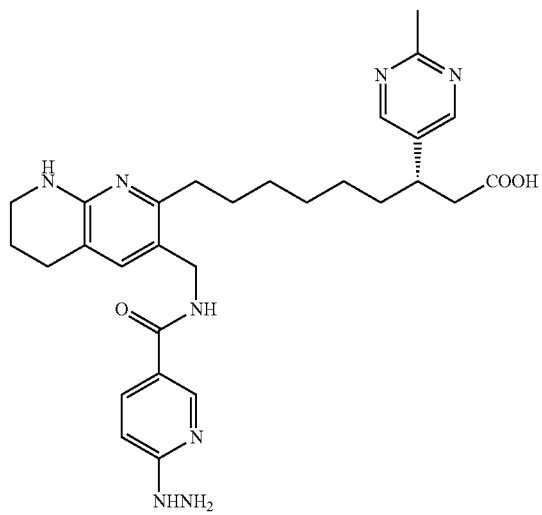

(E-14)

Hydrazine nicotinic acid succinimidyl ester (SoluLink, CA) (1-1.5 µmol) is added to a solution of compound 12 (~3 mg) and N-ethyl morpholine (10 µL) in DMSO (0.7 mL). The solution is aged at 20° C. for 1-2 hours. The product is precipitated by addition of 1:1 ethyl acetate/hexane (~10 mL) and washed with MTBE (2×5 mL). The solid is dissolved in water and purified by preparative HPLC and compound E-14 (appropriate salt form) isolated as a solid after evaporation of the preparative HPLC fraction.

For $^{99m}$Tc labeling the following protocol can be followed. 0.05 mL 1.0 N NaOH is added to a solution containing 70 mg tricine in 1.0 mL of water to raise the pH to 7. Then 0.1-1.0 mL of $^{99m}$TcO$_4^-$ in saline (10-100 mCi) is added, followed by 10 µg of the compound E-14 dissolved in 100 µL of 0.1 N HCl and 100 µg of SnCl$_2$. 2H$_2$O dissolved in 0.1 N HCl. The reaction is allowed to proceed at room temperature for 45 minutes. The product is analyzed by HPLC.

Example 15

Preparation of Hynic Conjugate of Compound 6 (E-15) and $^{99m}$Tc Labeling

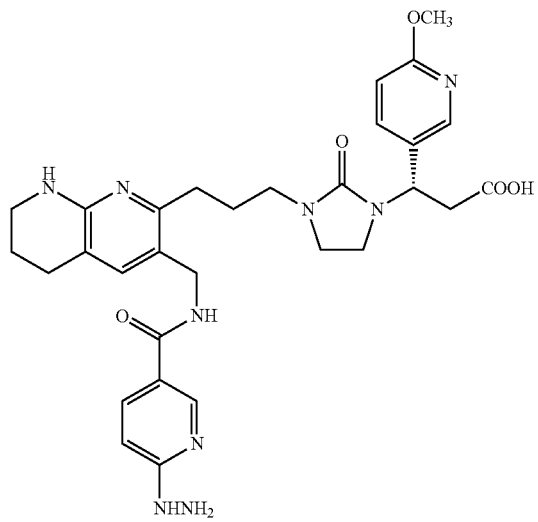

(E-15)

Hydrazine nicotinic acid succinimidyl ester (SoluLink, CA) (1-1.5 µmol) is added to a solution of compound 6 (~3 mg) and N-ethyl morpholine (10 µL) in DMSO (0.7 mL). The solution is aged at 20° C. for 1-2 hours. The product is precipitated by addition of 1:1 ethyl acetate/hexane (~10 mL) and washed with MTBE (2×5 mL). The solid is dissolved in water and purified by preparative HPLC and compound E-15 (appropriate salt form) isolated as a solid after evaporation of the preparative HPLC fraction.

$^{99m}$Tc labeling can be accomplished by the following protocol. 0.05 mL 1.0 N NaOH is added to a solution of 70 mg tricine in 1.0 mL of water to raise the pH to 7. Then 0.1-1.0 mL of $^{99m}$TcO$_4^-$ in saline (10-100 mCi) is added, followed by 10 µg of compound E15 dissolved in 100 µL of 0.1 N HCl and 100 µg of SnCl$_2$. 2H$_2$O dissolved in 0.1 N HCl. The reaction is allowed to proceed at room temperature for 45 minutes. The product is analyzed by HPLC.

Example 16

Preparation of DTPA Conjugate of Compound 12 (E-16) and $^{111}$In Labeling

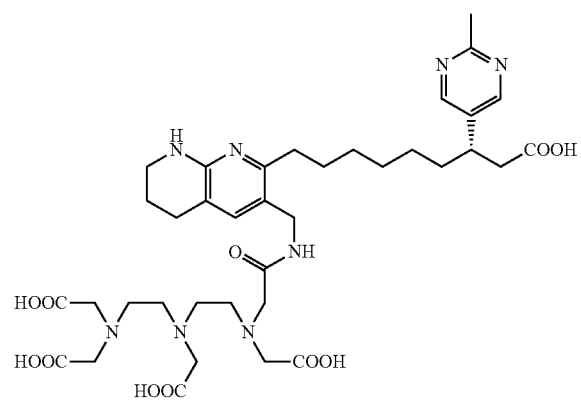

(E-16)

DTPA dianhydride (Aldrich) (1-1.5 µmol) is added to a solution of compound 12 (~3 mg) and N-ethyl morpholine (10 µL) in DMSO (0.7 mL). The solution is aged at 20° C. for 1-2 hours. The product is precipitated by addition of 1:1 ethyl acetate/hexane (~10 mL) and washed with MTBE (2×5 mL). The solid is dissolved in water and purified by preparative HPLC and compound E-16 is isolated as a solid after evaporation of the preparative HPLC fraction. About 50 µL of $^{111}$InCl$_3$ (about 100 mCi/mL in 0.05 M HCl) is combined with an equal volume of freshly prepared 1.0 M ammonium acetate, after which 0.1-1 mg of the compound E-16 dissolved in 0.25 mL water is added. The reaction is allowed to proceed at room temperature for 30 minutes. The product is analyzed by HPLC.

Example 17

Preparation of DTPA Conjugate of Compound 6 (E-17) and $^{111}$In Labeling

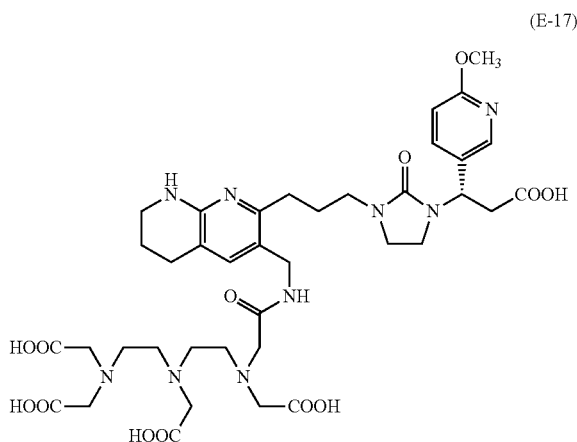 [SMILES: COc1ccc([C@H](CC(=O)O)N2CCN(CCCc3nc4c(cc3CNC(=O)CN(CCN(CCN(CC(=O)O)CC(=O)O)CC(=O)O)CC(=O)O)CCCN4)C2=O)cn1]

(E-17)

DTPA dianhydride (Aldrich) (1-1.5 µmol) is added to a solution of compound 6 (~3 mg) and N-ethyl morpholine (10 µL) in DMSO (0.7 mL). The solution is aged at 20° C. for 1-2 hours. The product is precipitated by addition of 1:1 ethyl acetate/hexane (~10 mL) and washed with MTBE (2×5 mL). The solid is dissolved in water and purified by preparative HPLC and compound E-17 isolated as a solid after evaporation of the preparative HPLC fraction. About 50 µL of $^{111}$InCl$_3$ (about 100 mCi/mL in 0.05 M HCl) is combined with an equal volume of freshly prepared 1.0 M ammonium acetate, after which 0.1-1 mg of compound E-17 dissolved in 0.25 mL water is added. The reaction is allowed to proceed at room temperature for 30 minutes. The product is analyzed by HPLC.

Example 18

Preparation of Bolton-Hunter Conjugate of Compound 12 (E-18)

$^{125}$I Bolton-Hunter reagent (Perkin Elmer/NEN) (1-1.5 µmol) is added to a solution of compound 12 (~3 mg) and N-ethyl morpholine (10 µL) in DMSO (0.7 mL). The solution is aged at 20° C. for 1-2 hours. The product is purified by preparative HPLC and E-18 isolated as a HPLC fraction.

Example 19

Preparation of Bolton-Hunter Conjugate of Compound 6 (E-19)

$^{125}$I Bolton-Hunter reagent (Perkin Elmer/NEN) (1-1.5 µmol) is added to a solution of compound 6 (~3 mg) and N-ethyl morpholine (10 µL) in DMSO (0.7 mL). The solution is aged at 20° C. for 1-2 hours. The product is purified by preparative HPLC and compound E-19 isolated as a HPLC fraction.

Example 20

Synthesis of Exemplary Fluorescent Metal Oxide Nanoparticles with Compound 12 (E-20)

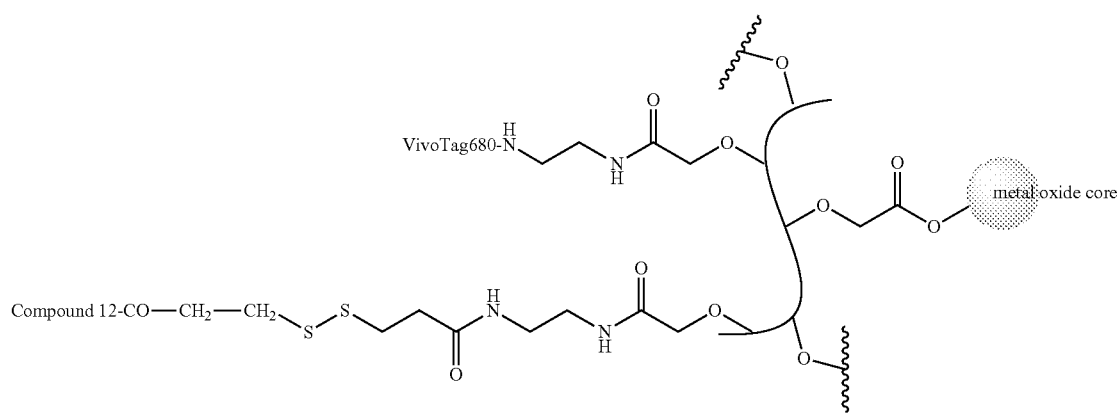

E-20

Amine functionalized fluorescent iron oxide nanoparticles (600 μL of 2.5 mg/mL iron) are combined with 50 μL of 0.1 M HEPES, pH 7 and 4 mg of succinimidyl pyridinedithiopropionate (SPDP) in 100 μL DMSO and rotated for 5 hours at room temperature. The particles are separated from unreacted SPDP by gel filtration eluting with 0.1 M HEPES, pH 7.0. Compound 12 modified with mercaptopropionic acid (1 mg) is dissolved in 100 μL DMSO and added to the SPDP conjugated particles, allowed to react at room temperature for 3 hours to produce the nanoparticles of compound E-20. The resulting nanoparticles (E-20) are purified by gel filtration using 1×PBS as an eluant.

Example 21

Preparation of Gadolinium Complex of DOTA Conjugated to Compound 12

The gadolinium complex of the conjugate of Example 12 is prepared according to the following procedure. 3-3.5 mg of the conjugate is dissolved in 2 mL 1 M ammonium acetate buffer at pH 7.0, and one equivalent $Gd(NO_3)_3$ solution (0.02 M in water) is added. The reaction mixture is heated at 100° C. for 30 minutes and the product is isolated by preparative HPLC. The fraction containing the complex is lyophilized. The identity of the complex is confirmed by mass spectroscopy.

Example 22

Synthesis of an Enzymatically Cleavable Oligopeptide Coupled to an Integrin Imaging Agent (Compound E-21)

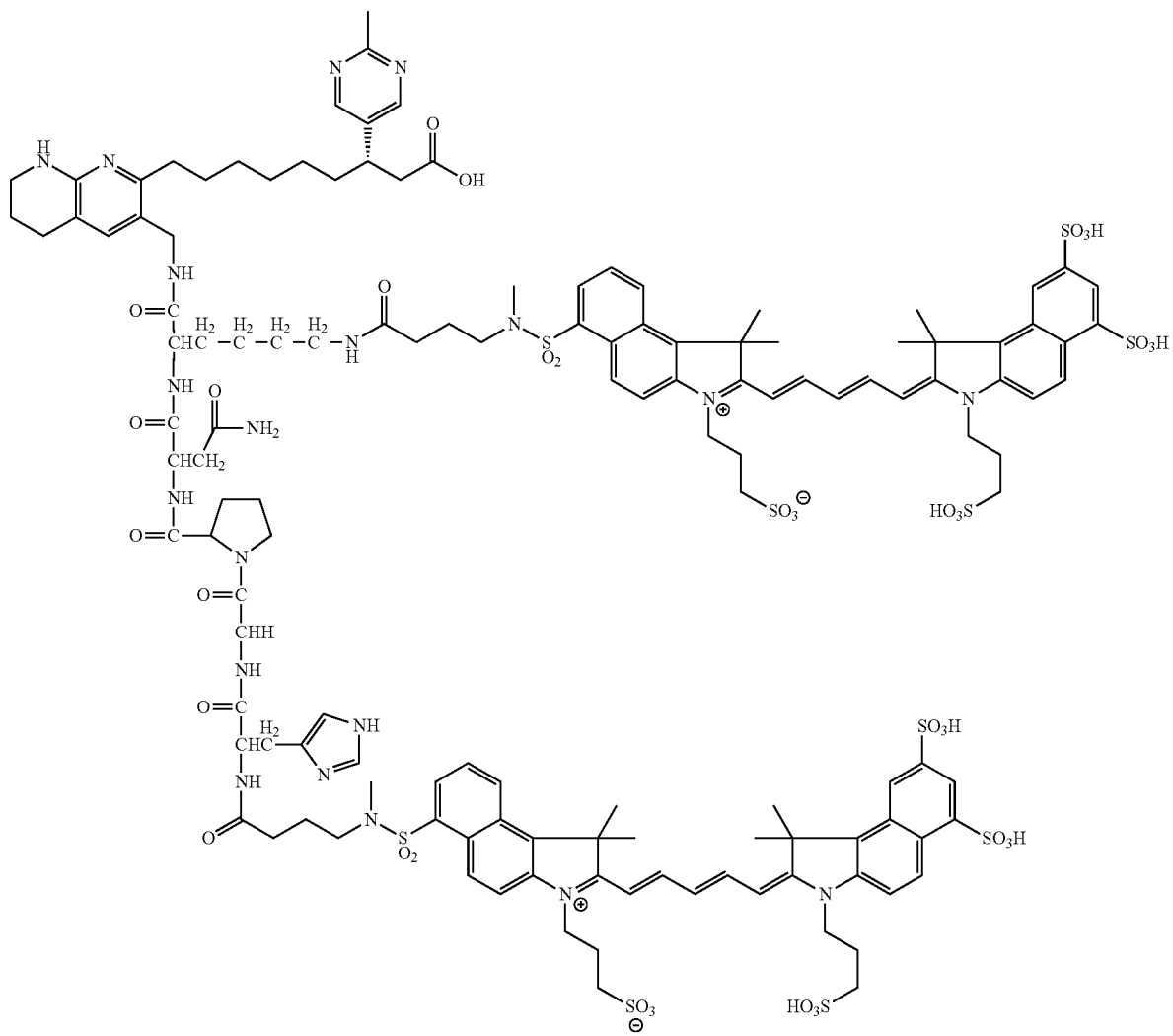

(E-21)

The peptide [H]-His-Gly-Pro-Asn-Lys-[OH] (SEQ ID No. 1) (Tufts University Core Facility, 0.45 μmol) and fluorophore C1 (see Table 2, 1.0 μmol) were combined in 100 μL of N,N-dimethylformamide (DMF) with 1 μL of N-methylmorpholine (NMM) and 0.25 mg of N,N-dimethylaminopyridine (DMAP). The solution was placed on a rotator shielded from light and rotated at room temperature for 16 hours. The doubly labeled peptide was precipitated by addition of 1.5 mL of methyl-t-butyl ether (MTBE) followed by centrifugation and decanting of the supernatant. The solid peptide was dried briefly under vacuum, dissolved in 200 μL of 0.1 M sodium bicarbonate and purified by HPLC and characterized by LC-MS.

Compound 12 (24 mg, 55 μmol) was dissolved in 1 mL of methanol and then 25 μL $SOCl_2$ was added. The solution was placed on a rotator and rotated at room temperature for 1 hour. The solvent was evaporated under vacuum. The solid product was redissolved in 2 mL methanol and evaporated under vacuum twice, then dissolved in 2 mL of 1:1 methanol/acetonitrile and evaporated under vacuum to yield the methyl ester of compound 12.

The methyl ester of compound 12 (0.8 mg, 2 μmol) was then combined with the labeled peptide (3.9 mg, 0.75 μmol) in 100 μL of N,N-dimethylformamide (DMF) with 1 μL of N-methylmorpholine (NMM). 1-ethyl-3-(3-dimethylaminopropyl) carbodiimide hydrochloride (EDC, 0.17 mg, 0.9 μmol) and hydroxybenzotriazole (HOBT, 0.17 mg, 1.2 μmol) were added and the solution was placed on rotator shielded from light and rotated at room temperature for 16 hours. The product was precipitated by addition of 1.5 mL of MTBE, isolated by centrifugation and decanting of the supernatant. The solid peptide was dried briefly under vacuum. To hydrolyze the ester, the solid was dissolved in 300 μL 0.1 M sodium hydroxide, and placed on a rotator shielded from light for 1 hr. The peptide was purified by HPLC and characterized by LCMS.

Example 23

Imaging of Tumors Using Exemplary Imaging Agents E-6 and E-7

This example shows that the compounds of the invention can be used to image tumors in vivo. In this experiment, NU/NU mice 6-8 weeks old (Charles River Laboratory, Wilmington, Mass.) were injected subcutaneously (s.c.) with 2×106 4T-1 cells bilaterally in each mammary fat pad. When tumors reached an approximate size of 3×3 mm (around 7 days after cell injection), mice were injected intravenously (i.v.) with 4 nmoles of each integrin agent (5 mice/probe+2 mice/no probe as control) in 100 μL volume via tail vein. Imaging was conducted 24 hours post-injection using a Fluorescence Molecular Tomography system (VisEn Medical, Bedford, Mass.). Examples of images using E-6 and E-7 are depicted in FIGS. 1 and 2, which show that the tumors can be imaged effectively.

Example 24

Inhibition of Cell Attachment to Vitronectin

This example shows that the compounds of the invention are selective for integrin $α_vβ_3$ over $α_vβ_5$, $α_5β_1$, and $α_{IIb}β_3$ in vitro. In this experiment, human embryonic kidney (HEK293) cells stably transfected with $α_vβ_3$ (HEK293-$α_vβ_3$ cells) were released with trypsin-EDTA and washed four times with serum-free MEM. Cells (25,000 cells/well) were added to microtiter wells coated with vitronectin and allowed to attach for 2 hours at 37° C. in a humidified incubator in the absence or presence of increasing concentrations of compound E-6 or unlabelled parent compound (as an inhibitor of E-6). Non-attached cells were gently washed away. Similar experiments were carried out with HEK293 cells stably transfected with $α_vβ_5$, $α_{IIb}β_3$, or $α_5β_1$. The attached cells were quantified by colorimetric detection of hexosaminidase enzymatic activity in a Vmax plate reader (Molecular Devices, Menlo Park, Calif.). The number of attached cells was quantified using a standard curve for each cell line assayed and expressed as a mean value of triplicate samples. The results are summarized in Table 4

TABLE 4

| | $IC_{50}$ (nM) | |
|---|---|---|
| | E-6 | Parent Compound |
| $α_vβ_3$ | 4.1 ± 0.3 | 0.82 ± 0.2 |
| $α_vβ_5$ | 33 | 1.3 ± 0.2 |
| $α_{IIb}β_3$ | 39 | >10,000 |
| $α_5β_1$ | >2,000 | >10,000 |

Table 4 depicts the $IC_{50}$ values for each experiment, which demonstrate that Compound E-6 exhibits stronger affinity for $α_vβ_3$ integrin compared to $α_{IIb}β_3$ and $α_vβ_5$ while no specific binding to $α_5β_1$ was detected. Compared to the parent compound, E-6 (i) exhibits a 5-fold loss of affinity to $α_vβ_3$, (ii) a 25-fold loss of affinity to $α_vβ_5$, (iii) retains higher potency in binding to $α_{IIb}β_3$, and (iv) exhibits little affinity for $α_5β_1$.

Example 25

Binding of Compound E-6 to HEK293-$α_vβ_3$ Cells

This example shows the affinity of E-6 for $α_vβ_3$. Cell binding assays using HEK293 cells stably expressing human $α_vβ_3$ were performed.

HEK293 cells stably transfected with $α_vβ_3$ (HEK293-$α_vβ_3$ cells) were plated onto poly-L-lysine coated Lab-Tek II chambered coverglass (Nunc, Rochester, N.Y.) the day before the assay. Cells were first incubated with DAPI (10 μg/ml) for 3 hours, followed by CellMask (Invitrogen, Carlsbad, Calif.) staining for 5 minutes. Cells were then washed 2× with PBS and incubated with E-6 (200 nM in PBS containing 5% serum) at 4° C. or 37° C. for 30 minutes. For the competition study, cells were incubated with parent compound (200 μM) for 1 hour before E-6 incubation. Confocal microscopy was performed on a Leica SP5 confocal system (Leica, Wetzlar, Germany).

FIG. 3 shows that compound E-6 binds to the receptors on the surface of the cells and the binding can be prevented by the parent compound. This demonstrates that compound E-6 binds to cells in an integrin-dependent manner. Co-localization of compound E-6 with the CellMask membrane marker indicates accumulation on the surface membrane. Receptor recycling (endocytosis) results in E-6 internalization at 37° C., but not at 4° C.

Example 26

Equilibrium Binding and Dissociation Measurements of Compound E-6

For equilibrium binding and dissociation measurements, HEK293-$α_vβ_3$ cells (1×10$^5$) were incubated with 0, 3.12, 6.25, 12.5, 20, 25, 40, 50, 80, 100, and 200 nM of compound E-6 at 4° C. for 30 minutes in "flow cytometric buffer" (145 nM NaCl, 5 mM KCl, 1 mM $MgCl_2$, and 10 mM HEPES ph 7.4). The amount of probe bound to integrins on HEK293-$\alpha_v\beta_3$ cells was determined by flow cytometry (FACSCalibur, BD Biosciences, CA). Data was analyzed using FlowJo software and $K_d$ values were calculated using SigmaPLot 10 software. For $k_{off}$ determination, HEK293-$\alpha_v\beta_3$ cells ($1\times10^6$) were incubated with 100 nM of E-6 at 4° C. for 30 minutes and labeled cells were than transferred into PBS containing 10 mM of parent compound. The amount of probe bound to the integrins on HEK293-$\alpha_v\beta_3$ cells was determined by flow cytometry (FACSCalibur, BD Biosciences, CA) before mixing with unlabeled compound, and 1, 1.5, 2.5, 3.5, 4.5, 5.5, and 24 hours after mixing. Data was analyzed using FlowJo software and $k_{off}$ and $t_{1/2}$ values calculated using SigmaPLot 10 software. The results are summarized in FIG. 4A and FIG. 4B.

FIG. 4A shows that E-6 dissociates from the $\alpha_v\beta_3$ receptors with the rate described by the dissociation rate constant $k_{off}=1.08\times10^{-4}$ $s^{-1}$ ($t_{1/2}=107$ min). FIG. 4B shows the value of the apparent equilibrium binding constant ($K_d$) to be 4.2±0.6 nM (using a single binding site model). The active conformation of $\alpha_v\beta_3$ integrin, facilitated by $Mn^{2+}$ ions, is present on the surfaces of tumor cells and new vessel cells. Binding isotherms in the absence or presence of $Mn^{2+}$ were practically identical, demonstrating that compound E-6 binds to the active form of integrin. This further supports the ability of compound E-6 to bind integrin-expressing cells.

Example 27

Pharmacokinetics and Biodistribution of Compound E-6 in Mice

This example shows the pharmacokinetics and biodistribution of compound E-6 in mice.

Twenty-four female retired breeder BALB/c mice (Charles River Laboratories, Wilmington, Mass.) received a bolus intravenous (i.v.) injection of compound E-6 (2 nmoles in PBS). Terminal blood samples were collected by cardiac puncture from each mouse (following carbon dioxide asphyxiation). Three mice were sampled for each time point. Plasma was collected by centrifugation, diluted 1:2 in DMSO and fluorescence read using a fluorescence plate reader (Molecular Devices, Sunnyvale, Calif.). Data was normalized to a standard curve (FIG. 5A) prepared with known concentrations of E-6. The concentration dependence of compound E-6 in plasma was fitted into a two compartmental model with a calculated $t(1)_{1/2}=6$ min and $t(2)_{1/2}=210$ min, where $t(1)_{1/2}$ represents free E-6 clearing quickly from circulation and $t(2)_{1/2}$ corresponds to clearance of bound E-6.

For the biodistribution studies, female NU/NU mice 6-8 weeks old (Charles River Laboratory, Wilmington, Mass.) were injected subcutaneously (s.c.) with A673 cells ($5\times10^6$) in the first mammary fat pads. Once tumors reached the desired volume (measured with calipers using the formula volume $mm^3=(length\times width^2)/2$), mice were injected i.v. with compound E-6 (2 nmoles). Mice were sacrificed by carbon dioxide asphyxiation 24 hr later and certain tissues removed, rinsed with saline, blotted dry, and the imaged on VisEn's FMT2500 using the reflectance mode. Regions of interest (ROIs) were drawn around each organ using the FMT Software and the mean fluorescence (reported as counts/energy) determined for each organ and normalized to the mean fluorescence in tumors taken to be 100%. The results are summarized in FIG. 5B, which shows that fluorescence is widely distributed into the tissues with the highest concentration found in tumors, followed by the liver, small intestine and skin.

Example 28

Binding of E-6 by Endothelial and A673 Tumor Cells In Vitro

This example shows that compound E6 binds to endothelial cells and A673 tumor cells.

Cell binding assays were performed using HUVEC (Human umbilical vein endothelial cells) and human rhabdomyosarcoma A673 tumor cells. HUVEC or A673 (50,000 cells) (ATCC, Manassas, Va.) were seeded unto 8-well Lab-Tek chamberslides (Nalge-Nunc International, Naperville, Ill.) and left to adhere overnight at 37° C. in a humidified atmosphere containing 5% $CO_2$. The following day, the medium was changed to fresh complete medium containing compound E-6 or free dye (20 nM), incubated for 30 minutes at 37° C., washed 2× with PBS and fixed with paraformaldehyde for 30 minutes at 4° C. Competition studies were performed by pre-incubating the cells for 5 minutes with parent compound (200 nM) before addition of E-6. The cells on the microscopy slides were then allowed to air dry protected from light. The slides were mounted with ProLong® Gold antifade reagent with DAPI (Molecular Probes, Eugene, Oreg.) and cured overnight at room temperature protected from light. Merged images of the nuclear staining (DAPI) and fluorescent signals were collected using fluorescence microscopy (Zeiss, Thornwood, N.Y.)

Significant fluorescent signal was observed for both HUVEC and A673 cells labeled with E-6 (FIGS. 6A and 6D, respectively). The observed fluorescence intensity resulting from HUVEC cells and A673 cells (FIGS. 6B and 6E, respectively) was reduced in the presence of a blocking dose of parent compound. Furthermore, reduced or no fluorescence was detected in HUVEC cells and A673 cells incubated with free dye (same dye used to synthesize E-6) only (FIGS. 6C and 6F, respectively). These results demonstrate that compound E-6 specifically binds to integrin-expressing tumor and endothelial cells.

Example 29

In Vivo Imaging and Quantification of E-6 Signal in A673 Tumor-Bearing Mice

This example shows the imaging and quantification of E-6 signal in tumor-bearing mice. Female NU/NU mice 6-8 weeks old (Charles River Laboratory, Wilmington, Mass.) were injected subcutaneously (s.c.) with A673 cells ($5\times10^6$) in the first mammary fat pads. Once tumors reached the desired volume (measured with calipers using the formula volume $mm^3=(length\times width^2)/2$), mice were injected i.v. with E-6 (2 nmoles) in the absence or presence of excess, competing parent compound (100 nmoles). Control mice received free dye. For in vivo imaging, mice were anesthetized by gas anesthesia (isoflurane/oxygen mixture), placed in the VisEn's FMT2500 system imaging chamber one at a time, and imaged.

Fluorescence was readily detected in tumors and the unlabeled parent compound effectively reduces the total amount of E-6 signal in tumors. Under the same imaging conditions, no detectable fluorescence was observed in the tumors of mice injected with free dye.

Figure 7:
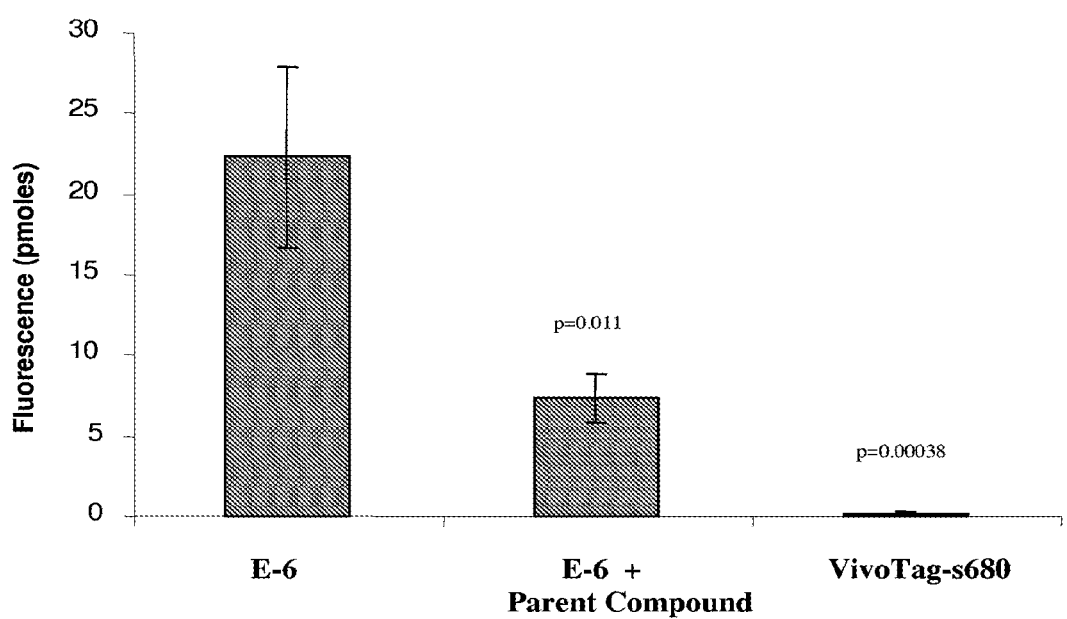
FIG. 7 is a bar chart depicting the detected fluorescence (in picomoles) from A673 tumor-bearing mice following administration of compound E-6, parent compound and compound E-6, or VivoTag s680 (free dye).

The fluorescent signal was quantified by drawing a three-dimensional ROI encompassing each tumor. As shown in FIG. 7, the total amount of E-6 fluorescence was significantly decreased in tumors of mice having received the parent compound (by 67%, p=0.011) or dye only (p=0.00038) as compared to tumors of mice injected with compound E-6. These results demonstrate the targeting specificity of using an integrin-sensing agent (E-6) in vivo.

Example 30

Effect of Anti-Angiogenic Avastin Treatment on Integrin and Cathepsin B Signals in A673 Tumor-bearing Mice This example demonstrates the effects of anti-angiogenic treatment on integrin and cathepsin B signals in A673 tumor-bearing mice.

A673 tumor-bearing mice were randomized once their tumors reached the desired volume and injected i.v. with either E-6 (2 nmoles) or free dye (2 nmoles). For competition studies, mice were injected with the parent compound (100 nmoles) followed 5 minutes later by compound E-6 (2 nmoles). For therapy studies, mice were treated with either 2 mg/kg Avastin (bevacizumab, Genentech, CA) or vehicle (PBS) intraperitoneally (i.p.) 2× week, and injected 7 days after beginning the treatment with 2 nmoles each of compound E-6 and ProSense (ProSense750, VisEn Medical, Bedford, Mass.) in a final volume of 200 μl PBS. ProSense is a protease-activatable fluorescence agent comprising fluorochromes linked to a peptide scaffold. Proteolytic cleavage of the scaffold by cathepsin B activity (and to a lesser extent cathepsins K, L, and S) releases the fluorochromes and results in extensive fluorescence (via dequenching). Imaging was performed 24 hours after administration of the agents using the FMT2500. Differential localization of fluorescent signal with compound E-6 and ProSense can be seen in the same animal. The wavelength of the laser was selected to 680 nm or 750 nm, corresponding to the absorption spectra of the fluorescent agents administered to the animal, enabling simultaneous imaging and quantification of 2 spectrally distinct agents.

Figure 8:
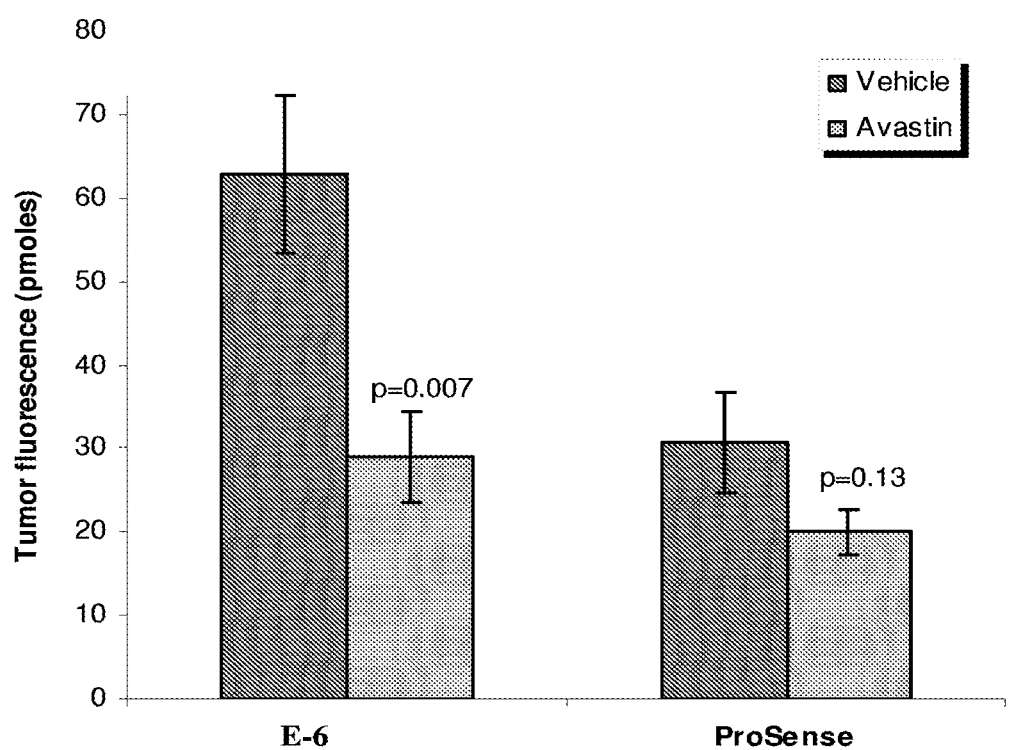
FIG. 8 is a bar chart showing the quantification of tumor fluorescence from A673 tumor-bearing mice injected with either compound E-6 or ProSense following treatment with Avastin or phosphate buffered saline (vehicle).

Following Avastin treatment, the signal produced by compound E-6 in tumors decreased by a greater amount than the signal produced by ProSense, demonstrating different modes of action for E-6 and ProSense (FIG. 8).

INCORPORATION BY REFERENCE

All publications, patents, and patent applications cited herein are hereby expressly incorporated by reference in their entirety and for all purposes to the same extent as if each was so individually denoted.

EQUIVALENTS

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. An integrin targeting agent comprising:
   (a) an integrin targeting moiety (ITM) comprising a molecule represented by Formula II:

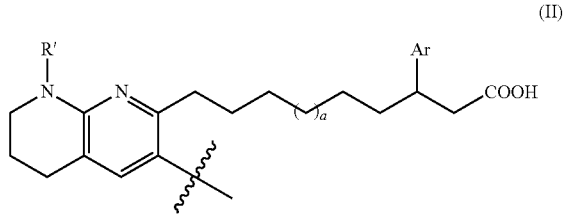

(II)

or Formula IV:

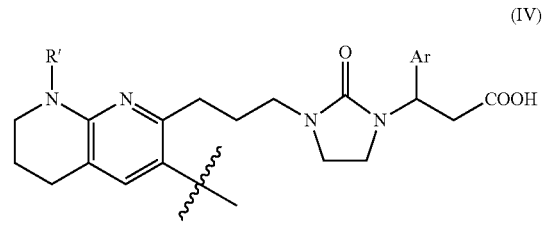

(IV)

wherein a is 0, 1, 2, or 3, Ar is an aryl or heteroaryl;
R' is H or alkyl;

and salts thereof; and (b) a reporter chemically linked, optionally through a linker (L) moiety, to the integrin targeting moiety via the bond denoted as ⌇ wherein the reporter is selected from the group consisting of a fluorophore reporter, a fluorochrome reporter, an optical reporter, a magnetic reporter, a radiolabel, an X-ray reporter, an ultrasound imaging reporter, or a nanoparticle-based reporter, or a combination thereof.

2. The agent of claim 1, wherein the agent comprises a plurality of integrin targeting moieties each chemically linked to the reporter.

3. The agent of claim 1, wherein the reporter is a fluorophore, a fluorochrome, an optical reporter, a magnetic reporter, a radiolabel, an X-ray reporter, an ultrasound imaging reporter or a nanoparticle reporter.

4. The agent of claim 1, wherein the alkyl is substituted with a substituted or unsubstituted, monocyclic or bicyclic, heteroaryl moiety.

5. The agent of claim 1 further comprising a biological modifier chemically linked to the integrin targeting moiety, the reporter or the optional linker.

6. An integrin targeting agent represented by Formula I:

$$((ITM-L)_m-L_n-IR_q)-BM_g \quad (I)$$

wherein,

ITM represents a molecule represented by Formula II:

(II)

or Formula IV:

(IV)

wherein a is 0, 1, 2, or 3, Ar is an aryl or heteroaryl;
R' is H or alkyl;
and salts thereof;
L, independently for each occurrence, represents a bond or a linker moiety;
IR represents an imaging reporter;

m represents an integer between 1 to 500, n represents an integer between 0 to 500, q represents an integer between 1 to 500, and g represents an integer between 0 to 500; and BM represents a biological modifier.

7. The agent of claim 1, wherein Ar is a monocyclic heteroaryl, bicyclic heteroaryl, moncyclic aryl or bicyclic aryl; optionally substituted with 1, 2, or 3 moieties each independently selected from the group consisting of H, halo, alkoxy, alkyl, aryl, and heteroaryl.

8. The agent of claim 1, wherein Ar is selected from the group consisting of

9. The agent of claim 6, wherein the ITM is represented by Formula IIA:

(IIA)

wherein a is 0, 1, 2, or 3, Ar is an aryl or heteroaryl;
R' is H or alkyl;
and salts thereof.

10. The agent of claim 1, wherein ITM is represented by Formula III:

(III)

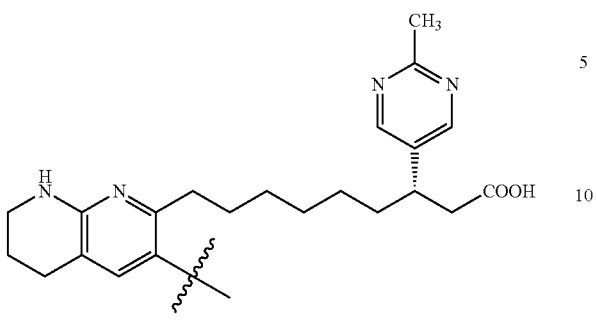

and salts thereof.

11. The agent of claim 1, wherein the ITM is represented by Formula IVA:

(IVA)

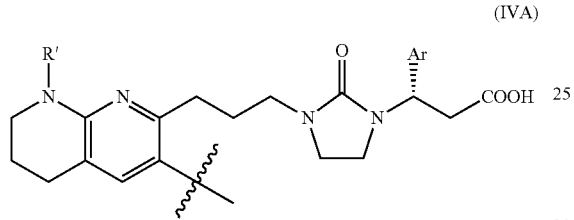

wherein Ar is an aryl or heteroaryl and R' is H or alkyl.

12. The agent of claim 1, wherein ITM is a compound is represented by Formula V:

(V)

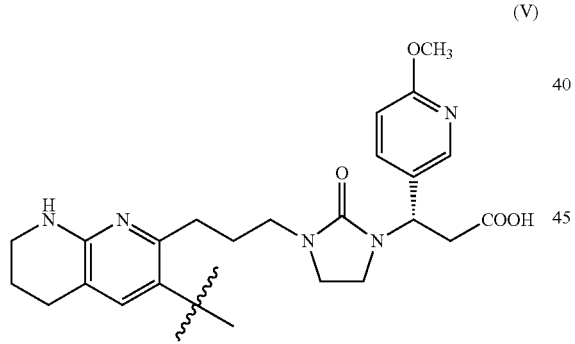

and salts thereof.

13. The agent of claim 1, wherein the reporter is a far-red or a near-infrared fluorochrome.

14. The agent of claim 1, wherein the reporter is a carbocyanine fluorochrome or an indocyanine fluorochrome.

15. The agent of claim 1, wherein the reporter is represented by Formula VIII:

(VIII)

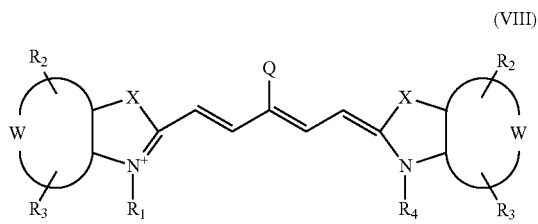

or a salt thereof, wherein:

X is independently, for each occurrence, selected from the group consisting of $C(CH_2Y_1)(CH_2Y_2)$, O, S, and Se;

$Y_1$ and $Y_2$ are independently selected from the group consisting of H, $C_1$-$C_{20}$ aliphatic group, optionally substituted with —OR*, N(R*)$_2$ or —SR*, wherein R* is H or alkyl;

W is selected from the group consisting of a benzo-condensed, a naphtho-condensed or a pyrido-condensed ring;

$R_1$ is selected from the group consisting of $(CH_2)_xCH_3$, $(CH_2)_ySO_3^-$ and $(CH_2)_ySO_3H$, wherein x is an integer selected from 0 to 6 and y is an integer selected from 2 to 6;

$R_4$ is selected from the group consisting of $(CH_2)_xCH_3$, $(CH_2)_ySO_3^-$ and $(CH_2)_nSO_3H$, wherein x is an integer selected from 0 to 6 and y is an integer selected from 2 to 6;

$R_2$ and $R_3$ are each independently selected, for each occurrence, from the group consisting of H, carboxylate, carboxylic acid, carboxylic ester, amine, amide, sulfonamide, hydroxyl, alkoxyl, a sulphonic acid moiety and a sulphonate moiety;

Q is selected from a group consisting of a heteroaryl ring substituted with a carboxyl group or 6-membered heteroaryl ring substituted with a carbonyl group.

16. The agent of claim 1, wherein the reporter is a fluorochrome represented by Formula IX:

(IX)

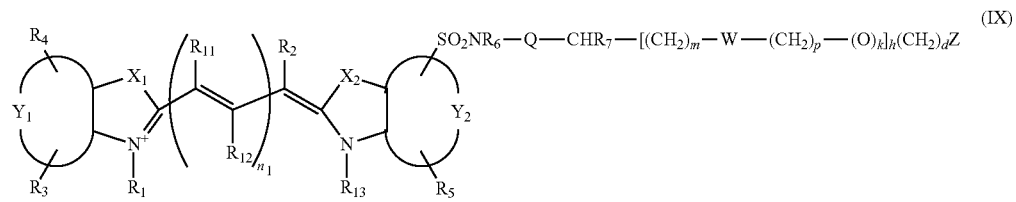

or a salt thereof, wherein:

X$_1$ and X$_2$ are independently selected, for each occurrence from the group consisting of C(CH$_2$K$_1$)(CH$_2$K$_2$), O, S and Se;

K$_1$ and K$_2$ are independently selected from the group consisting of H, a C$_1$-C$_{20}$ aliphatic group optionally substituted with —OR*, N(R*)$_2$ or —SR*; or K$_1$ and K$_2$ together form part of a substituted or unsubstituted carbocyclic, or heterocyclic ring;

Y$_1$ and Y$_2$ are each independently a benzo-condensed ring, a naphtha-condensed ring or a pyrido-condensed ring;

n$_1$ is 1, 2, or 3;

R$_2$, R$_{11}$ and R$_{12}$ are independently selected from the group consisting of H, F, Br, Cl, C$_1$-C$_6$ alkyl, C$_1$-C$_6$ alkoxy, aryloxy, a nitrogen-containing heterocyclic ring, a nitrogen-containing heteroaromatic ring, a sulfonate, an iminium ion, or any two adjacent R$_{12}$ and R$_{11}$ substituents or R$_2$ and R$_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by C$_1$-C$_6$ alkyl, halogen, or OR* or SR*;

R$_1$ and R$_{13}$ are (CH$_2$)$_x$CH$_3$, when x is an integer selected from 0 to 6; or R$_1$ and R$_{13}$ are independently (CH$_2$)$_n$SO$_3^-$ or (CH$_2$)$_n$SO$_3$H when n is an integer selected from 2 to 6;

R$_3$, R$_4$ and R$_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is absent, or is selected from a carbonyl moiety or a substituted or unsubstituted C$_1$-C$_6$ alkyl group, wherein 0-2 of the methylene groups of the alkyl group is optionally be replaced by NH, O or S, or a substituted or unsubstituted C$_1$-C$_6$ carbocyclic, non-aromatic carbocyclic, heterocyclic or non-aromatic heterocyclic ring wherein the heterocyclic rings contains 1-2 heteroatoms;

R$_6$ is selected from the group consisting of: H, substituted or unsubstituted C$_1$-C$_{20}$ aliphatic group, a substituted or unsubstituted aryl, a substituted or unsubstituted alkylaryl, wherein R$_6$ is optionally substituted with halogen, OR*, N(R*)$_2$ or SR*, R$_7$ is selected from the group consisting of H, a substituted or unsubstituted C$_1$-C$_{20}$ aliphatic group, a substituted or unsubstituted aryl, a substituted or unsubstituted alkylaryl, wherein R$_7$ is optionally substituted with halogen, OR*, N(R*)$_2$ or SR*; or R$_6$ and R$_7$, taken together form a 4-, 5-, 6- or 7-membered heterocyclic or non-aromatic heterocyclic ring optionally substituted with halogen, OR*, N(R*)$_2$ or SR*; or NR$_6$, Q and CHR$_7$ together form a substituted or unsubstituted or heterocyclic or non-aromatic heterocyclic ring system wherein the rings contain 1 or 2 heteroatoms, wherein rings are optionally substituted with —OR*, N(R*)$_2$ or —SR*; and W is absent or is a group selected from the group consisting of —SO$_2$NR$_6$—Q—CHR$_7$—, —O—, —COO—, and —CONH—;

h=0-70; k=0 or 1; d=0-12; m=0-12; p=0-12;

Z is a N, O or S nucleophile; and each R* is independently —H or C$_{1-20}$ alkyl.

17. The agent of claim 1, wherein the reporter is a radiolabel comprising a radioisotopic metal selected from the group consisting of copper, gallium, indium, technetium, yttrium, and lutetium.

18. The agent of claim 1, wherein the reporter is selected from the group consisting of $^{99m}$Tc, $^{111}$In, $^{64}$Cu, $^{67}$Ga, $^{186}$Re, $^{188}$Re, $^{153}$Sm, $^{177}$Lu, and $^{67}$Cu.

19. The agent of claim 1, wherein said reporter is a radiolabel comprising a therapeutic radiopharmaceutical.

20. The agent of claim 19, wherein the therapeutic radiopharmaceutical is a radioisotopic metal selected from the group consisting of $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rb, $^{111}$Ag, and $^{192}$Ir.

21. The agent of claim 1, wherein the reporter is a magnetic reporter selected from the group consisting of Gd(III), Dy(III), Fe(III), Mn(II) and metal oxide nanoparticles.

22. The agent of claim 1, wherein the reporter is an X-ray contrast agent.

23. The agent of claim 1, wherein L comprises a moiety selected from the group consisting of an amido, amino-polyethylene glycol-carboxylic acid, amino-polyethylene glycol azide, diaminoPEG, cysteic acid, glutamic acid, aminocaproic acid, ethylenediamine, propylenediamine, spermidine, spermine, hexanediamine, and a diamine-amino acid, such as homolysine, lysine, ornithine, diaminobutyric acid and diaminopropionic acid, succinic acid, glutaric acid, suberic acid, or adipic acid.

24. The agent of claim 1, wherein L comprises an enzymatically-cleavable oligopeptide comprising from about 2 to 15 amino acids.

25. The agent of claim 24, wherein L comprises an enzymatically cleavable bond and one reporter is covalently linked to an oligopeptide sequence located at one side of the enzymatically cleavable bond and one reporter is covalently linked to an oligopeptide sequence located at the other side of the enzymatically cleavable bond.

26. The agent of claim 24, wherein the agent comprises at least two fluorochromes that quench one another or a fluorochrome and a quencher each located at fluorescence quenching permissive sites on the agent, whereupon cleavage of the oligopeptide results in dequenching of at least one fluorochrome.

27. The agent of claim 5, wherein the biological modifier (BM) is selected from the group consisting of a PEG, phospholipid, amino acid, peptide, phospholipid PEG, carbohydrate, sulfonate, polysulfonate, glutamic acid, cysteic acid, naphthylalanine, phenylalanine, diphenylpropylamine, 4,4-diphenylcyclohexanol, glucosamine, mannosamine, galactosamine, arginine, lysine, homolysine, leucine, and combinations thereof.

28. An integrin imaging agent selected from the group consisting of
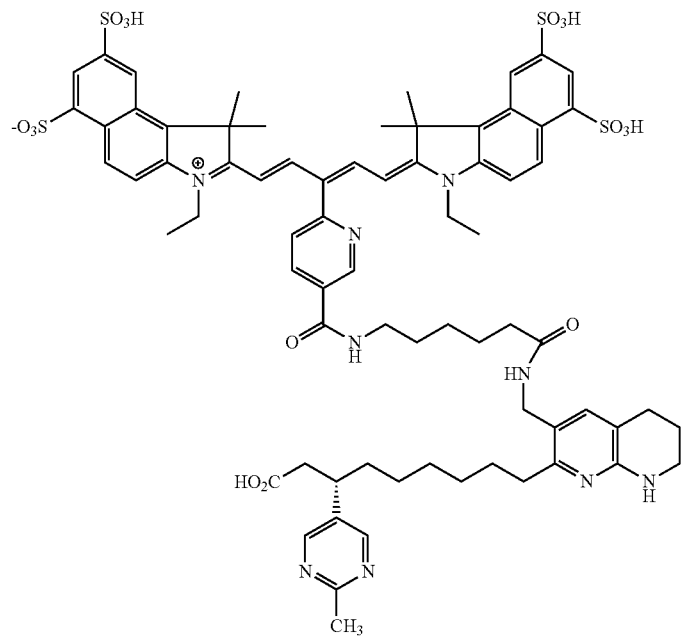
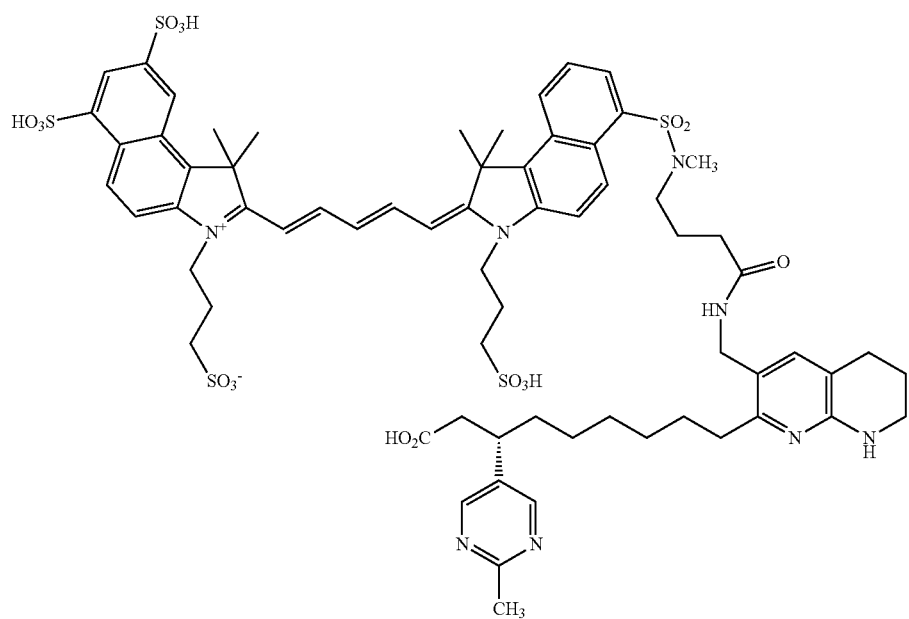

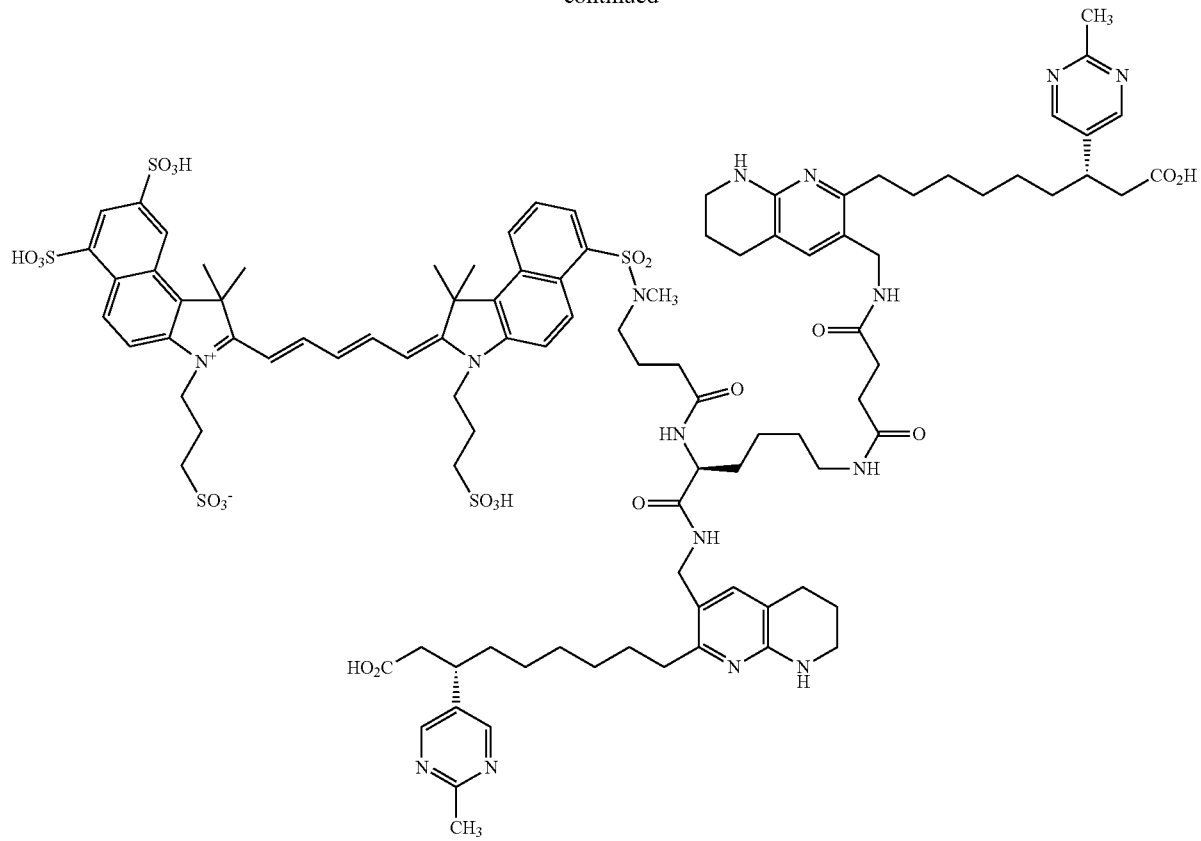

and pharmaceutically acceptable salts thereof.

29. A pharmaceutically acceptable composition suitable for administration to a subject comprising an agent of claim 1 and a pharmaceutically acceptable excipient.

30. A method of in vivo imaging, the method comprising:
(a) administering to a subject an agent of claim 1;
(b) allowing the agent to distribute within the subject; and
(c) detecting a signal emitted by the agent.

31. A method of in vivo optical imaging, the method comprising:
(a) administering to a subject an agent of claim 1, wherein the agent comprises a fluorochome;
(b) allowing the agent to distribute within the subject;
(c) exposing the subject to light of a wavelength absorbable by the fluorochrome; and
(d) detecting a signal emitted by the agent.

32. The method of claim 30, wherein the signal emitted by the agent is used to construct an image.

33. The method of claim 32, wherein the image is a tomographic image.

34. The method of claim 30, wherein steps (a)-(c) are repeated at predetermined time intervals thereby to permit evaluation of the emitted signals of the integrin agent in the subject over time.

35. The method of claim 31, wherein steps (a)-(d) are repeated at predetermined time intervals thereby to permit evaluation of the emitted signals of the integrin agents in the subject over time.

36. The method of claim 30, wherein the subject is an animal or a human.

37. The method of claim 30, wherein in step (a) two or more imaging probes whose signal properties are distinguishable from one another are administered to a subject, wherein at least one of the imaging probes is an integrin binding agent.

38. The method of claim 31, wherein the illuminating and detecting steps are performed using an endoscope, catheter, tomographic system, hand-held optical imaging system, or an intraoperative microscope.

39. The method of claim 30, wherein the presence, absence, or level of emitted signal is indicative of a disease state.

40. The method of claim 30, wherein the method is used to detect and/or monitor a disease selected from the group consisting of bone disease, cancer, cardiovascular disease, atherosclerosis, restinosis, cardiac ischemia, myocardial reperfusion injury, environmental disease, dermatological disease, immunologic disease, inherited disease, infectious disease, inflammatory disease, metabolic disease, neurodegenerative disease, ophthalmic disease, and respiratory disease.

41. The method of claim 30, wherein, in step (a), cells labeled with the integrin binding agent are administered to the subject.

42. The method of claim 41, wherein the signal emitted by the integrin binding agent is used to monitor trafficking and localization of the cells.

43. A method of imaging angiogenesis in a subject, the method comprising the steps of:
(a) administering to a subject an agent of claim 1; and
(b) detecting the presence of the agent to generate an image representative of new blood vessel formation in the subject.

44. A method of treating a disease in a subject comprising administering to a subject, either systemically or locally, an agent of claim 1, wherein the agent comprises a radiolabel that localizes in the disease area and delivers an effective dose of radiation.

45. An in vitro imaging method, the method comprising:
(a) contacting a sample with an agent of claim 1;
(b) allowing the agent to bind to a biological target, if present in the sample;
(c) optionally removing unbound agent; and
(d) detecting signal emitted from the agent to determine whether the agent has been activated by or bound to the biological target.

46. The method of claim 45, wherein the sample is a biological sample.

```
SEQUENCE LISTING

<160> NUMBER OF SEQ ID NOS: 1

<210> SEQ ID NO 1
<211> LENGTH: 5
<212> TYPE: PRT
<213> ORGANISM: Artificial sequence
<220> FEATURE:
<223> OTHER INFORMATION: recombinant/synthetic peptide

<400> SEQUENCE: 1

His Gly Pro Asn Lys
1               5
```